(12) United States Patent
Yue

(10) Patent No.: US 10,667,841 B2
(45) Date of Patent: Jun. 2, 2020

(54) METHOD AND DEVICE FOR ENDOSCOPIC GRAFT DELIVERY USING A SLOTTED CANNULA

(71) Applicant: Vertical Spine LLC, Wall, NJ (US)

(72) Inventor: James J. Yue, Guilford, CT (US)

(73) Assignee: Vertical Spine LLC, Wall, NJ (US)

( * ) Notice: Subject to any disclaimer, the term of this patent is extended or adjusted under 35 U.S.C. 154(b) by 144 days.

(21) Appl. No.: 15/816,649

(22) Filed: Nov. 17, 2017

(65) Prior Publication Data

US 2018/0140327 A1 May 24, 2018

Related U.S. Application Data

(60) Provisional application No. 62/423,908, filed on Nov. 18, 2016.

(51) Int. Cl.
| | |
|---|---|
| *A61B 17/34* | (2006.01) |
| *A61B 17/88* | (2006.01) |
| *A61B 17/16* | (2006.01) |
| *A61B 17/70* | (2006.01) |
| *A61B 17/17* | (2006.01) |
| *A61F 2/46* | (2006.01) |
| *A61B 17/02* | (2006.01) |

(52) U.S. Cl.
CPC ...... *A61B 17/3439* (2013.01); *A61B 17/1635* (2013.01); *A61B 17/3417* (2013.01); *A61B 17/707* (2013.01); *A61B 17/7022* (2013.01); *A61B 17/7037* (2013.01); *A61B 17/7083* (2013.01); *A61B 17/8805* (2013.01); *A61B 17/0218* (2013.01); *A61B 17/1757* (2013.01); *A61B 17/3421* (2013.01); *A61F 2/4601* (2013.01)

(58) Field of Classification Search
CPC .......... A61F 2/4601; A61B 2017/3445; A61B 17/3415; A61B 17/3468; A61B 17/3421
See application file for complete search history.

(56) References Cited

U.S. PATENT DOCUMENTS

| | | | | |
|---|---|---|---|---|
| 5,275,611 A | * | 1/1994 | Behl | A61B 17/34 600/585 |
| 2003/0065333 A1 | * | 4/2003 | DeMayo | A61B 17/7095 606/92 |
| 2017/0340455 A1 | * | 11/2017 | Greter | A61B 17/56 |

* cited by examiner

*Primary Examiner* — Julianna N Harvey

(74) *Attorney, Agent, or Firm* — Sughrue Mion, PLLC

(57) ABSTRACT

A method may include inserting, through a slotted cannula, a first anchor assembly into a first spinal segment. The first anchor assembly may be attached to a suture at a first end of the suture. The method may include inserting, through the slotted cannula, a second anchor assembly into a second spinal segment. The method may include extruding, through the slotted cannula, a graft construct to permit the graft construct to extend from the first spinal segment to the second spinal segment. The graft construct may be connected to the suture. The method may include attaching, using the slotted cannula, a second end of the suture to the second anchor assembly to permit a spinal fusion of the first spinal segment and the second spinal segment using the graft construct.

6 Claims, 29 Drawing Sheets

METHOD AND DEVICE FOR ENDOSCOPIC GRAFT DELIVERY USING A SLOTTED CANNULA

CROSS-REFERENCE TO RELATED APPLICATION

This application claims priority under 35 U.S.C. § 119 to U.S. Provisional Application No. 62/423,908, filed on Nov. 18, 2016, the contents of which are incorporated by reference in their entirety.

BACKGROUND

Spinal fusion, also known as spondylodesis or spondylosyndesis, is a neurosurgical or orthopedic technique that connects (e.g., joins, links, fuses, etc.) two or more vertebrae. Spinal fusion may be performed at any level of the spine (e.g., cervical, thoracic, and/or lumbar) and prevents movement between the fused vertebrae. Spinal fusion may involve a bone grafting technique (e.g., using autografts, allografts, and/or composite materials) to assist fusion of the vertebrae.

SUMMARY

According to some possible implementations, a method may include inserting, through a slotted cannula, a first anchor assembly into a first spinal segment. The first anchor assembly may be attached to a suture at a first end of the suture. The method may include inserting, through the slotted cannula, a second anchor assembly into a second spinal segment. The method may include extruding, through the slotted cannula, a graft construct to permit the graft construct to extend from the first spinal segment to the second spinal segment. The graft construct may be connected to the suture. The method may include attaching, using the slotted cannula, a second end of the suture to the second anchor assembly to permit a spinal fusion of the first spinal segment and the second spinal segment using the graft construct.

According to some possible implementations, a cannula system may include a cannula. The cannula system may include a slot extending longitudinally from a proximal end of the cannula to a distal end of the cannula. The cannula system may include a channel extending longitudinally from the proximal end of the cannula to the distal end of the cannula. The cannula system may permit a first guidewire to be inserted into a first spinal segment through the cannula. The cannula system may permit a first anchor assembly to be inserted into the first spinal segment over the first guidewire while a blade, extending through the channel, is inserted into a third spinal segment. The cannula system may permit a second guidewire to be inserted into a second spinal segment through the cannula. The cannula system may permit a second anchor assembly to be inserted into the second spinal segment through the cannula and over the second guidewire. The cannula system may permit a graft construct to be extruded through the cannula and extend from the first spinal segment to the second spinal segment. The cannula system may translate, using the slot, from the first spinal segment to the second spinal segment without removing the first guidewire.

According to some possible implementations, a method may include inserting a first anchor into a first spinal segment through a cannula. The method may include inserting a second anchor into a second spinal segment through the cannula. The method may include extruding a graft construct through the cannula to permit the graft construct to extend from the first spinal segment to the second spinal segment. The method may include attaching, through the cannula, a suture to permit a spinal fusion of the first spinal segment and the second spinal segment using the graft construct.

DETAILED DESCRIPTION OF THE
PREFERRED EMBODIMENT

The following detailed description of example implementations refers to the accompanying drawings. The same reference numbers in different drawings may identify the same or similar elements.

During spinal fusion surgery, a surgeon places a grafting material within a space between a set of spinal vertebrae. Often, the surgeon uses metal plates, rods, screws, and/or other hardware to hold the vertebrae together such that the vertebrae can heal and fuse into a single unit. The surgeon is often required to make a relatively large incision to permit the grafting material and hardware to be inserted into the patient, and to permit the surgeon to perform the procedure. The number, size, and nature of incisions can produce deleterious effects. Similarly, the length and subjectivity of the spinal fusion procedure can negatively affect the outcome of the procedure, increase the amount of required recovery time, etc.

Some implementations described herein provide for endoscopic graft delivery using a slotted cannula. As such, some implementations described herein provide a minimally invasive technique that reduces a size of a required incision, reduces an amount of time associated with a spinal fusion procedure, reduces dependency on individual experience of the operating surgeon, and/or the like. In this way, some implementations described herein improve the safety, efficacy, accuracy, consistency, and/or the like, of spinal fusion procedures.

Figure 1:
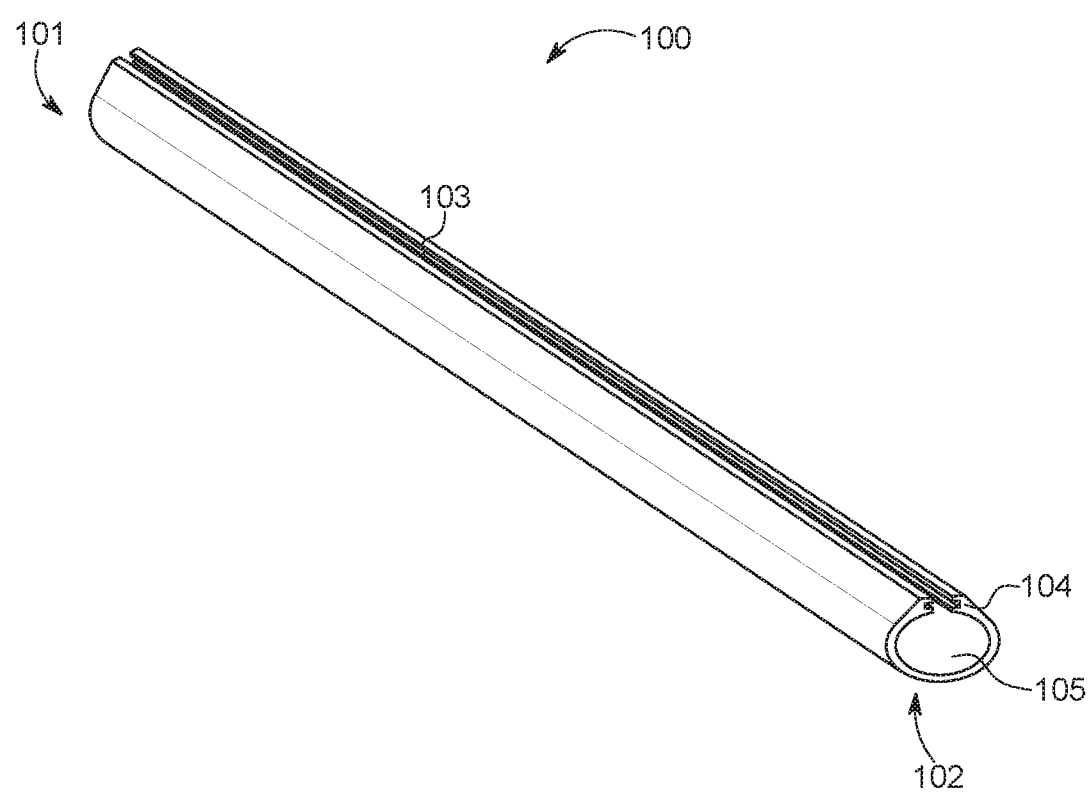
FIG. 1 is an isometric view of a slotted cannula described herein.

FIG. 1 is an isometric view of a slotted cannula 100 described herein. As shown in FIG. 1, slotted cannula 100 may include a proximal end 101, a distal end 102, a longitudinal slot 103, a longitudinal channel 104, and a cavity 105. Slotted cannula 100 may include a component configured to access a spinal segment through an incision. For example, slotted cannula 100 may include a cannula, a tube, a device including a hollow cavity, and/or the like.

As used herein, a spinal segment may refer to a vertebra, a portion of a vertebra, and/or the like. For example, a spinal segment may refer to a transverse process, a spinous process, a vertebral foramen, an articular process, a lateral mass, a facet, a vertebral body, and/or the like.

Longitudinal slot 103 may be configured to permit slotted cannula 100 to translate laterally with respect to a guidewire such that the guidewire may enter and/or exit cavity 105 of slotted cannula 100 via longitudinal slot 103. In this way, some implementations described herein reduce a need of a surgeon to remove slotted cannula 100 through an incision to permit lateral translation of slotted cannula 100 with respect to a guidewire. Thereby, some implementations described herein reduce an amount of time, increase safety, increase accuracy, and/or the like, of spinal fusion procedures.

Longitudinal channel 104 may be configured to permit a blade to be inserted into and/or removed from slotted cannula 100. For example, a blade may be slidable, in a longitudinal direction of slotted cannula 100, within longitudinal channel 104. Longitudinal channel 104 may be substantially planar and include a width that corresponds to a width of a blade that is configured to be inserted into longitudinal channel 104.

Cavity 105 may be configured to permit various components to be inserted into, extruded from, and/or removed from slotted cannula 100. For example, cavity 105 may permit an endoscope, a guidewire, an anchor assembly, an anchor driver, a graft construct, a graft pusher, a suture tool, and/or the like, to be inserted into slotted cannula 100 and access a spinal segment through slotted cannula 100.

Slotted cannula 100 may be comprised of any suitable material to permit access to a spinal segment through an incision. For example, slotted cannula 100 may be comprised of a composite polymeric, a thermoplastic, an alloy, and/or the like. Additionally, or alternatively, slotted cannula 100 may include any suitable dimensions to permit access of a spinal segment through an incision.

As an example, and as shown in FIG. 1, slotted cannula 100 may include a substantially cylindrical shape, and include an outer diameter of 11.5 millimeters (mm) and an inner diameter of 9.5 mm. Additionally, as an example, longitudinal slot 103 may include a width of 1.5 mm, 2 mm, and/or the like. It should be understood that implementations described herein are applicable to many other types of configurations than as shown in FIG. 1.

Figure 2:
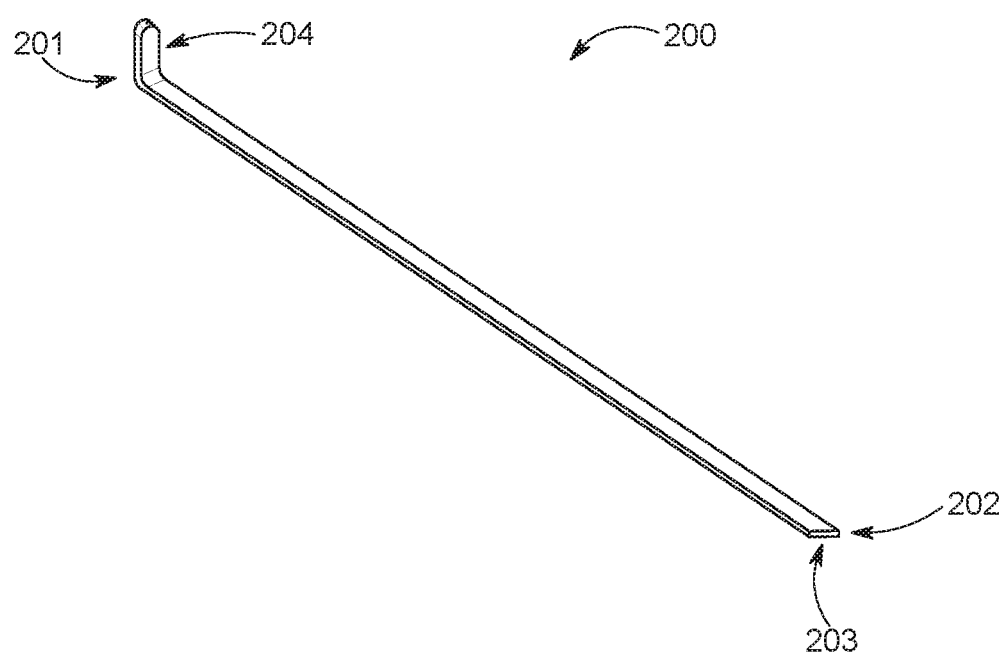
FIG. 2 is an isometric view of a blade described herein.

FIG. 2 is an isometric view of a blade 200 described herein. As shown in FIG. 2, blade 200 may include a proximal end 201, a distal end 202, a tip 203, and a tab 204. Blade 200 may include a component configured to permit slotted cannula 100 to be anchored to a spinal segment. For example, blade 200 may include a blade, a pin, a wire, and/or the like.

Tip 203 of blade 200 may be configured to permit blade 200 to be inserted into a spinal segment. For example, tip 203 may include a substantially sharp edge of blade 200 that permits blade 200 to be inserted into a spinal segment and/or to anchor slotted cannula 100.

Tab 204 may be configured to permit blade 200 to be manipulated within longitudinal channel 104 of slotted cannula 100. Additionally, or alternatively, tab 204 may be configured to anchor blade 200 within longitudinal channel 104 of slotted cannula 100.

Blade 200 may be inserted into longitudinal channel 104 of slotted cannula 100. For example, distal end 202 of blade 200 may be inserted into longitudinal channel 104 at proximal end 101 of slotted cannula 100. Additionally, or alternatively, distal end 202 of blade 200 may be translated longitudinally towards distal end 102 of slotted cannula 100. Additionally, or alternatively, tab 204 may prevent further insertion of blade 200 into longitudinal channel 104 of slotted cannula 100. Blade 200 may be removed from longitudinal channel 104 by manipulation of tab 204. For example, blade 200 may be completely removable with respect to longitudinal channel 104 of slotted cannula 100. Alternatively, blade 200 may be partially removable and/or displaceable with respect to longitudinal channel 104.

Blade 200 may be comprised of any suitable material for permitting slotted cannula 100 to be anchored to a spinal segment. For example, blade 200 may be comprised of an alloy, a metal, a composite plastic, and/or the like. Additionally, or alternatively, blade 200 may include any suitable dimensions for permitting slotted cannula 100 to be anchored to a spinal segment. Blade 200 may be configured to be disposed within longitudinal channel 104 of slotted cannula 100, and thereby may include dimensions that permit blade 200 to be inserted into and/or removed from longitudinal channel 104.

Figure 3:
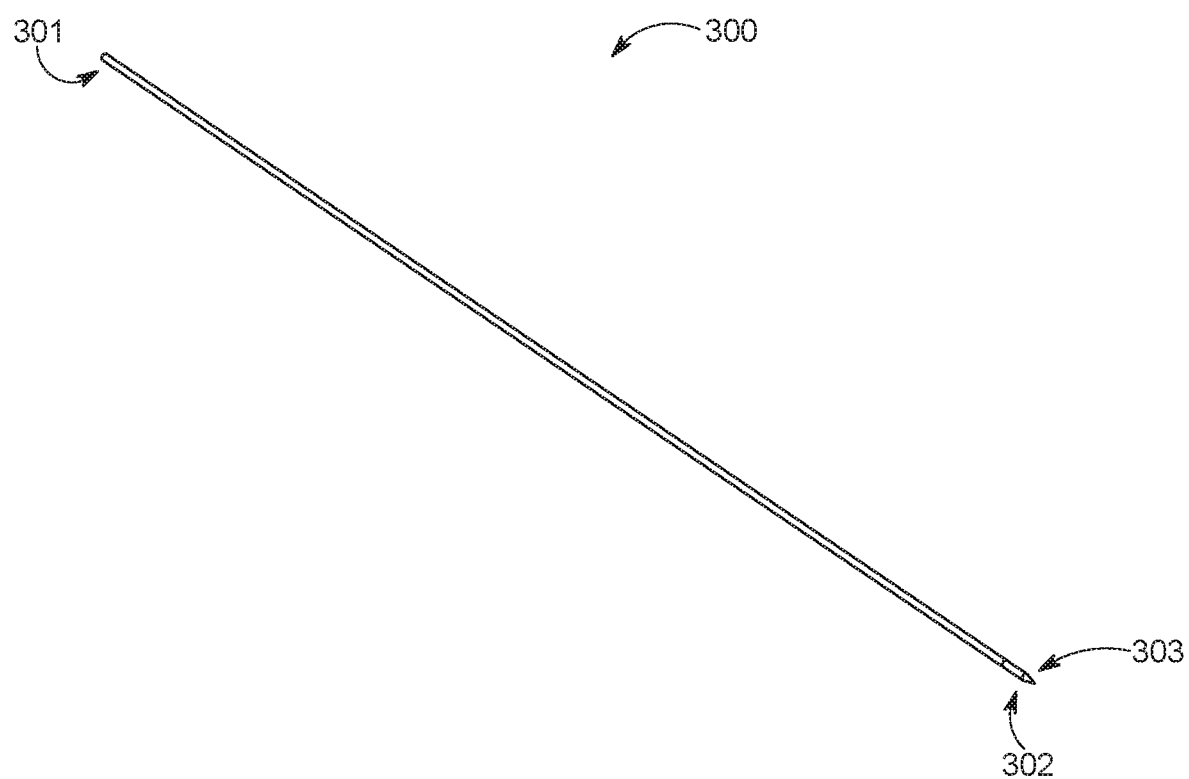
FIG. 3 is an isometric view of a guidewire described herein.

FIG. 3 is an isometric view of a guidewire 300 described herein. As shown in FIG. 3, guidewire 300 may include a proximal end 301, a distal end 302, and a tip 303. Guidewire 300 may include a component configured to be inserted into a spinal segment and/or guide an anchor assembly into a spinal segment. For example, guidewire 300 may include a wire, a pin, a rod, and/or the like. As particular examples, guidewire 300 may include a Kirschner wire (K-wire), a Steinmann pin, and/or the like.

Guidewire 300 may be comprised of any suitable material and/or may include any suitable dimensions to permit a screw assembly to be inserted into a spinal segment. For example, guidewire 300 may be comprised of a steel, an alloy, a composite plastic, and/or the like, and may include a diameter of 1 mm, 2 mm, 2.5 mm, etc., and/or a length of 9 mm, 11 mm, etc.

Figure 4:
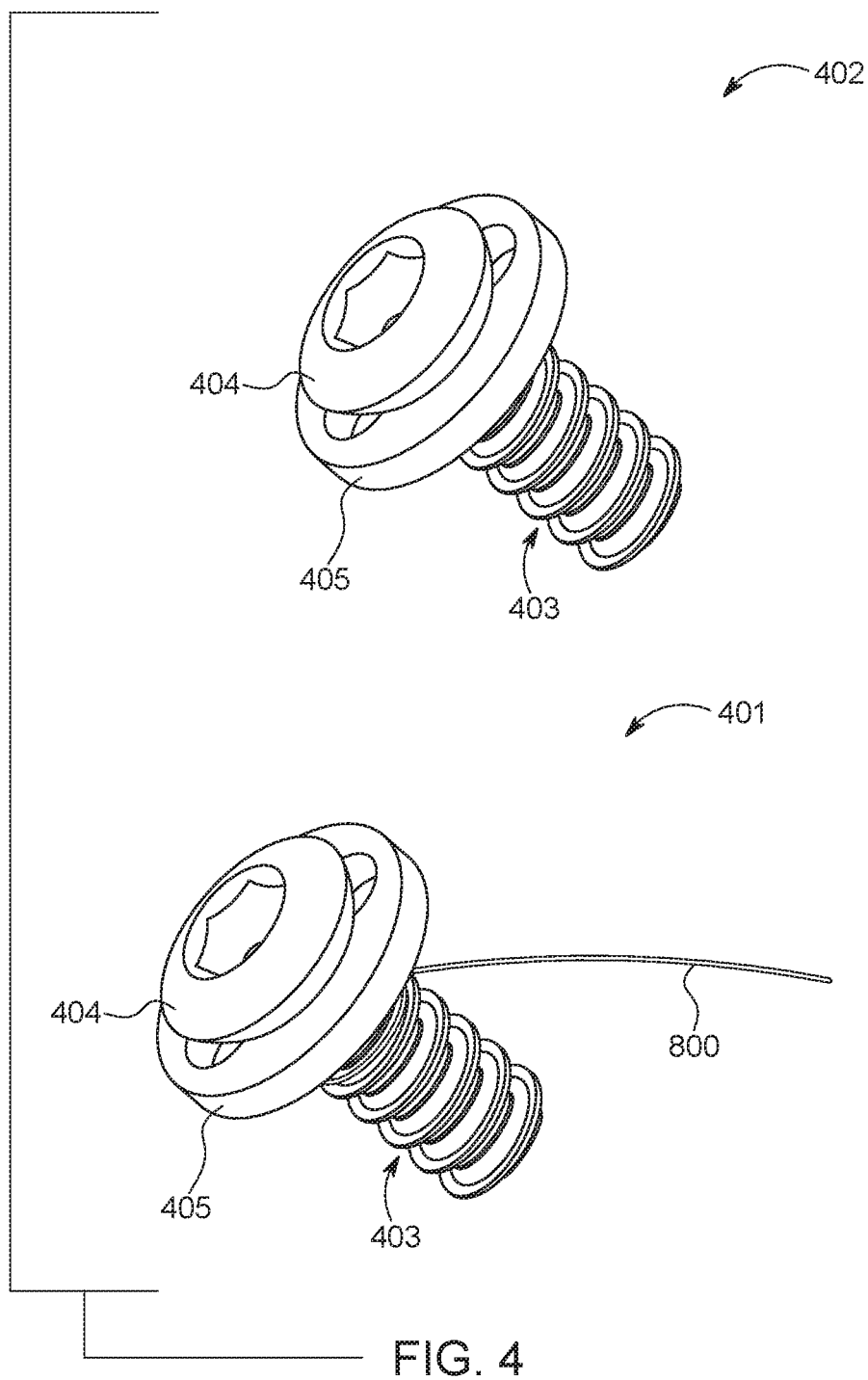
FIG. 4 is an isometric view of a set of anchor assemblies described herein.

FIG. 4 is an isometric view of a first anchor assembly 401 and a second anchor assembly 402 described herein. As shown in FIG. 4, first anchor assembly 401 may include an anchor portion 403, a head portion 404, a washer 405, and an attached suture 800. As further shown in FIG. 4, second anchor assembly 402 may include an anchor portion 403, a head portion 404, and a washer 405.

First anchor assembly 401 and/or second anchor assembly 402 may include a component configured to anchor a graft construct to a first spinal segment and/or a second spinal segment. For example, first anchor assembly 401 and/or second anchor assembly 402 may include a screw, a pin, a nail, a rod, a wire, an adhesive component, and/or the like.

Anchor portion 403 may include a cavity such that anchor portion 403 is hollow. Additionally, anchor portion 403 may be configured to be inserted over guidewire 300 and/or translate longitudinally with respect to guidewire 300.

Head portion 404 may be configured to connect with an anchor driver to permit the anchor driver to cause anchor portion 403 to be inserted into a spinal segment and/or fasten to the spinal segment. Head portion 404 may include any suitable drive type, such as a slot, a Phillips, a square, a Robertson, a hex, a torx, a spline, and/or the like.

Washer 405 may be configured to permit first anchor assembly 401 and/or second anchor assembly 402 to remain anchored with respect to a spinal segment. Additionally, or alternatively, washer 405 may be configured to permit suture 800 to be anchored with respect to first anchor assembly 401 and/or second anchor assembly 402.

Washer 405 may include first dimensions in association with first anchor assembly 401, and include second dimensions in association with second anchor assembly 402. For example, a first washer 405 associated with first anchor assembly 401 may be larger than a second washer 405 associated with second anchor assembly 402. In this way, and as described elsewhere herein, suture 800 may more easily be wrapped around second anchor assembly 402 because the second washer 405 is relatively smaller.

First anchor assembly 401 may include an attached suture 800. For example, and as shown in FIG. 4, suture 800 may be fastened to first anchor assembly below a bottom surface of washer 405 and around anchor portion 403. Suture 800 may be attached to first anchor assembly 401 prior to first anchor assembly 401 being inserted into a first spinal segment, as described elsewhere herein.

First anchor assembly 401 and/or second anchor assembly 402 may be comprised of any suitable material and/or may include any suitable dimensions to permit first anchor assembly 401 and/or second anchor assembly 402 to be anchored with respect to a spinal segment and/or anchor suture 800 with respect to a spinal segment.

Figure 5:
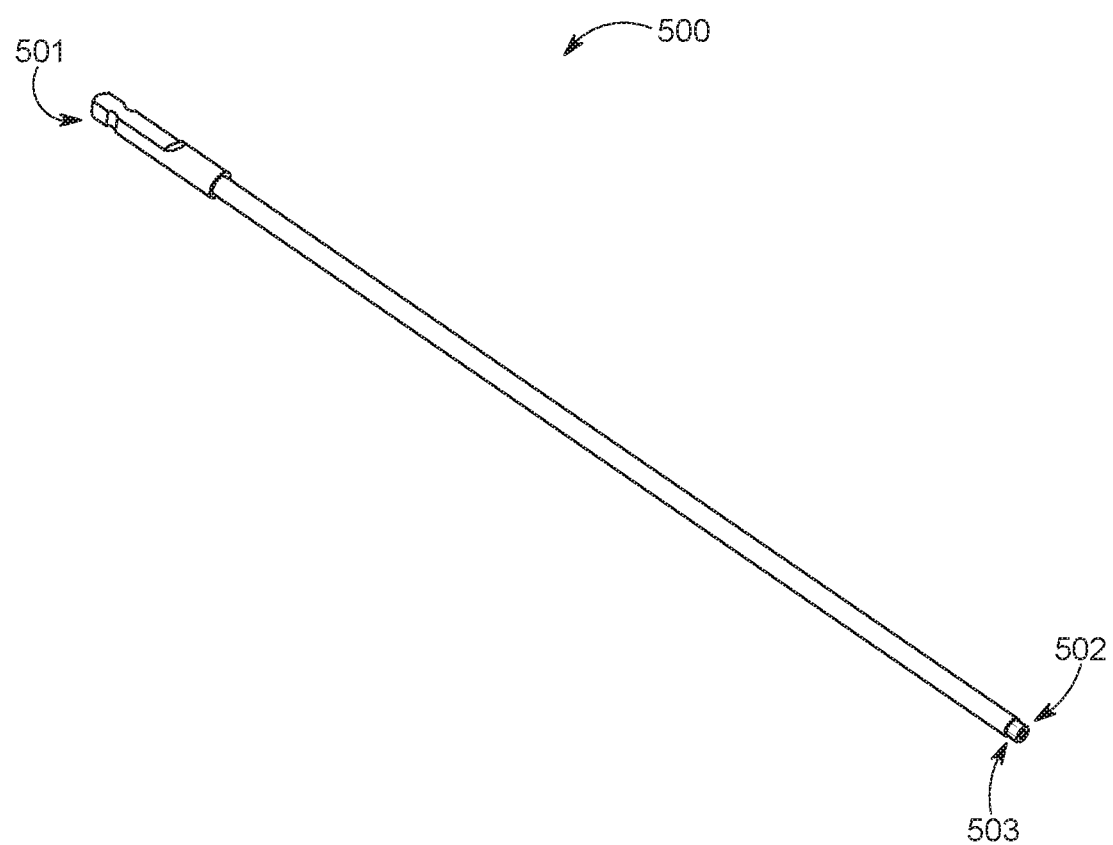
FIG. 5 is an isometric view of an anchor driver described herein.

FIG. 5 is an isometric view of an anchor driver 500 described herein. As shown in FIG. 5, anchor driver 500 may include a proximal end 501, a distal end 502, and a tip 503. Anchor driver 500 may include a component configured to cause first anchor assembly 401 and/or second anchor assembly 402 to be anchored with respect to a spinal segment. For example, anchor driver 500 may include a driver including tip 503 having a drive type that corresponds to a drive type of head portion 404 of first anchor assembly 401 and/or second anchor assembly 402. Anchor driver 500 may be comprised of any suitable material and/or may include any suitable dimensions to cause first anchor assembly 401 and/or second anchor assembly 402 to be anchored with respect to a spinal segment.

Figure 6:
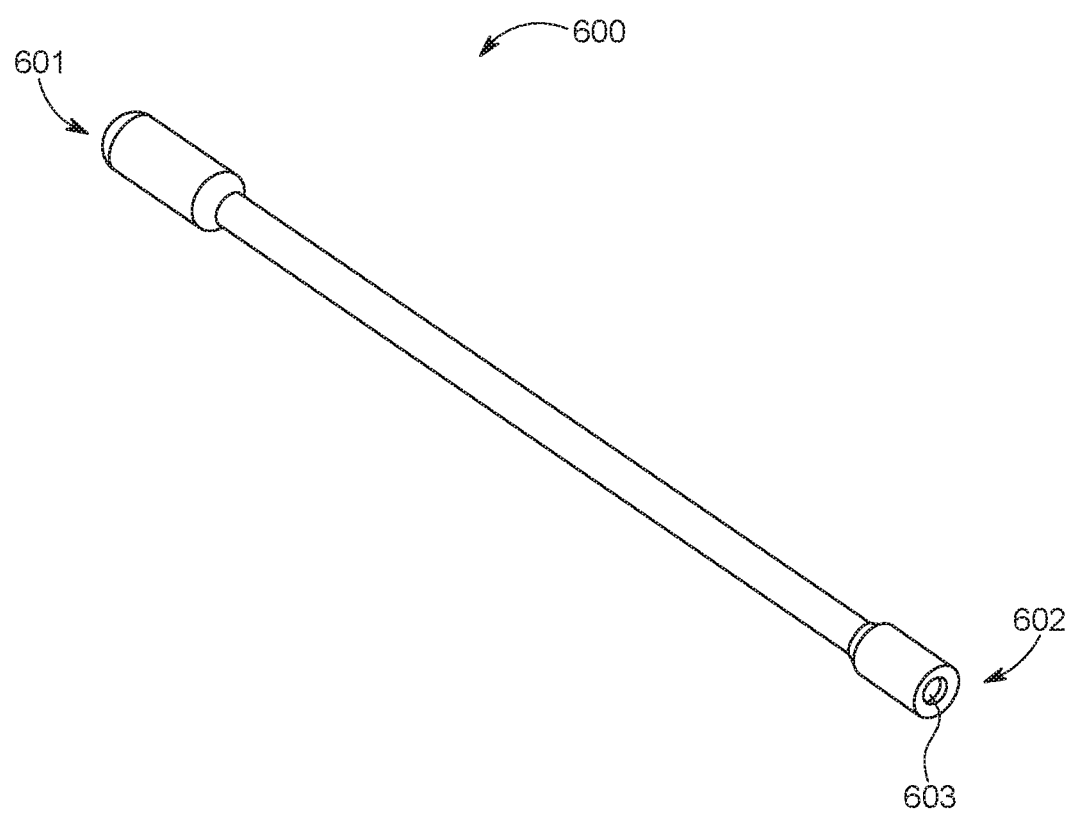
FIG. 6 is an isometric view of a graft pusher described herein.

FIG. 6 is an isometric view of a graft pusher 600 described herein. As shown in FIG. 6, graft pusher 600 may include a proximal end 601, a distal end 602, and a cavity 603. Graft pusher 600 may include a component configured to cause a graft construct to be extruded from cavity 105 of slotted cannula 100. For example, graft pusher 600 may include a rod, a wire, a cylinder, and/or the like. Cavity 603 of graft pusher 600 may be configured to permit a suture tool to be inserted into graft pusher 600.

Graft pusher 600 may be comprised of any suitable material and/or may include any suitable dimensions to permit graft pusher 600 to cause a graft construct to extrude from slotted cannula 100.

Figure 7:
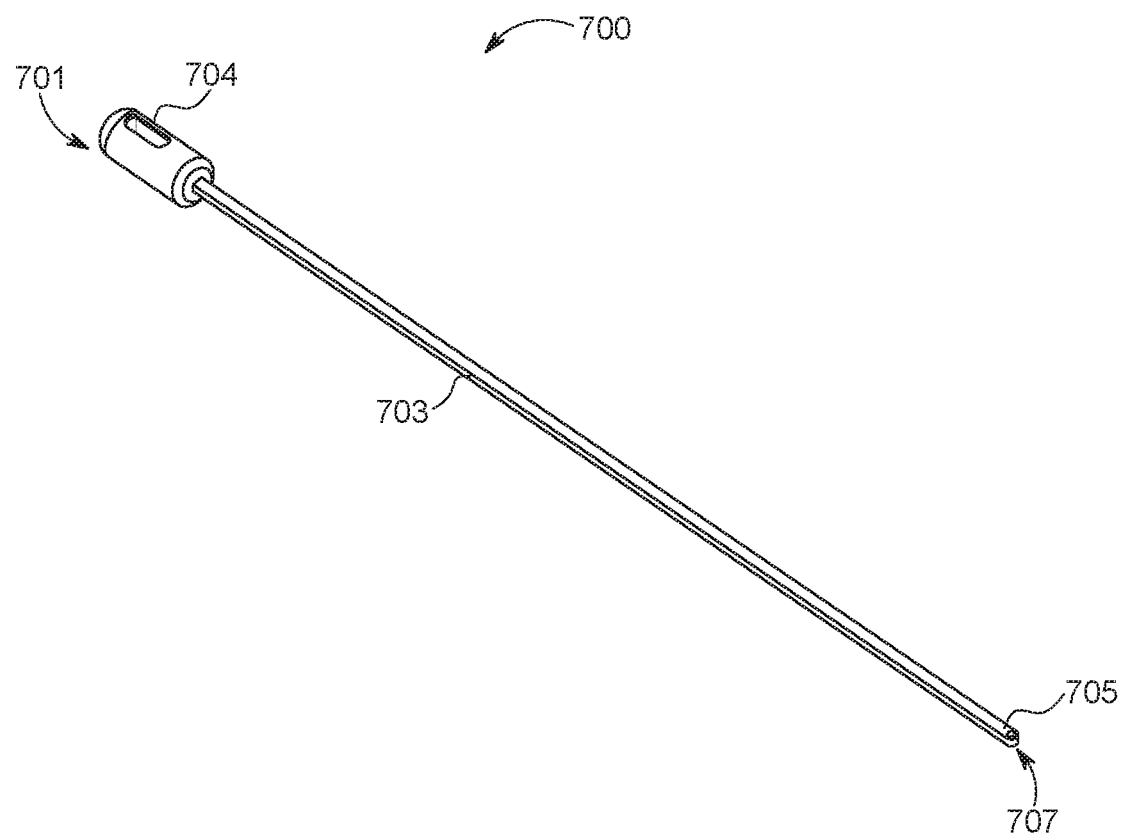
FIG. 7 is an isometric view of a suture tool described herein.

FIG. 7 is an isometric view of a suture tool 700. As shown in FIG. 7, suture tool 700 may include a proximal end 701, a distal end 702, a longitudinal portion 703, a proximal connection mechanism 704, and a distal connection mechanism 705.

Suture tool 700 may include a component configured to permit manipulation of suture 800. For example, suture tool 700 may include a rod, a cylinder, a wire, and/or the like. Longitudinal portion 703 may be configured to be inserted into cavity 603 of graft pusher 600 such that longitudinal portion 703 is capable of being disposed within cavity 603 of graft pusher 600. Proximal connection mechanism 704 may be configured to clamp suture 800 to permit suture 800 to be manipulated by suture tool 700. Additionally, or alternatively, distal connection mechanism 705 may be configured to clamp suture 800 to permit suture to be manipulated by suture tool 700. Suture tool 700 may be comprised of any suitable material and/or may include any suitable dimensions to permit manipulation of suture 800.

Figure 8:
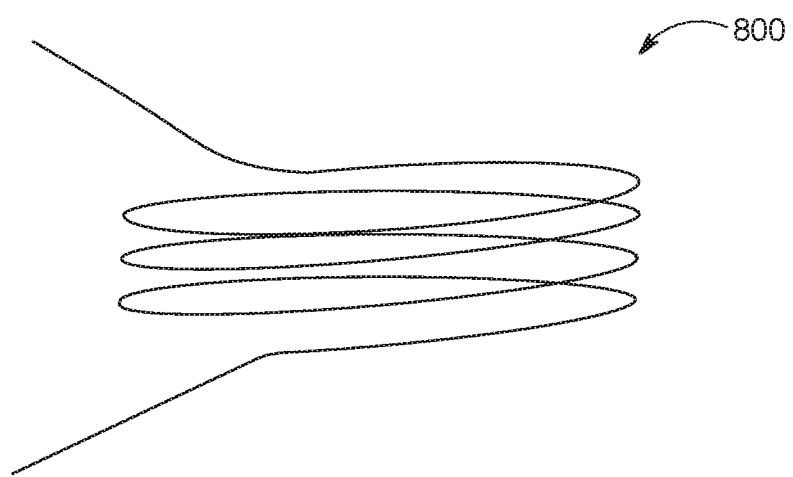
FIG. 8 is an isometric view of a suture described herein.

FIG. 8 is an isometric view of a suture 800 described herein. Suture 800 includes a component configured to attach a graft construct to first anchor assembly 401 and/or second anchor assembly 402.

Suture 800 may be comprised of any suitable material for attaching a graft construct to first anchor assembly 401 and/or second anchor assembly 402. For example, suture 800 may be comprised of nylon, polyester, polyvinylidene fluoride, polyglycolic acid, polydioxanone, and/or the like.

Suture 800 may include any suitable dimensions for attaching a graft construct to first anchor assembly 401 and/or second anchor assembly 402. For example, suture 800 may include any suitable diameter, gauge, and/or the like. As examples, suture 800 may include a diameter of 0.02 mm, 0.05 mm, 0.3 mm, and/or the like.

Figure 9:
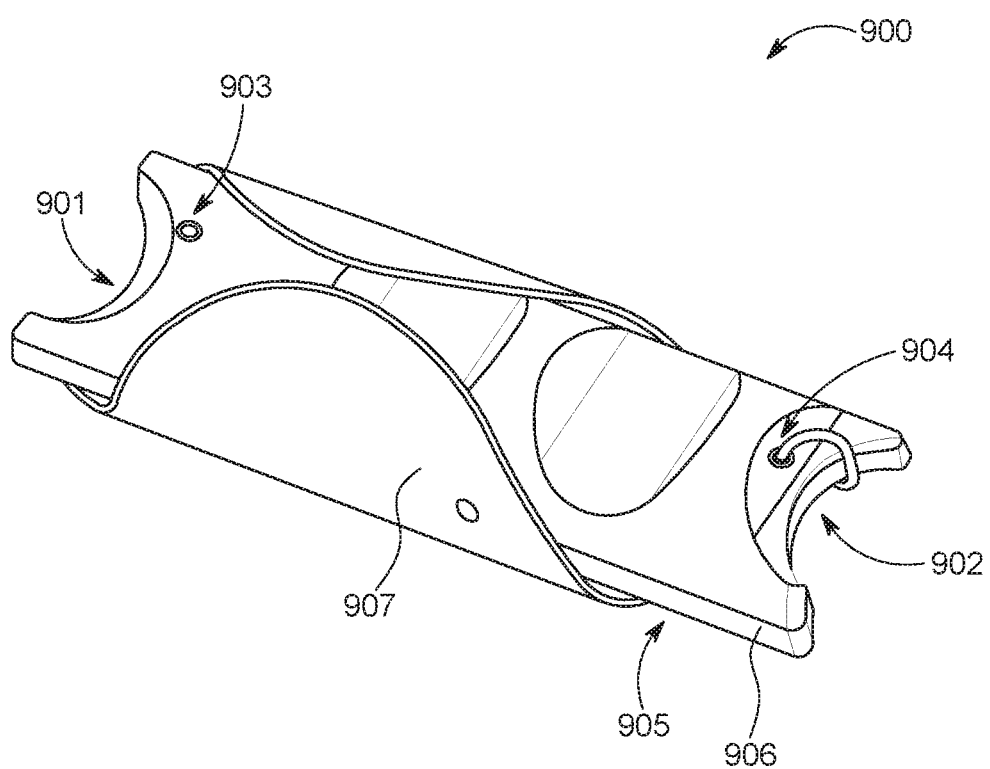
FIG. 9 is an isometric view of a graft construct described herein.

FIG. 9 is an isometric view of a graft construct 900 described herein. As shown in FIG. 9, graft construct 900 may include a first end 901, a second end 902, a first connection mechanism 903, a second connection mechanism 904, a lower graft portion 905, an upper graft portion 906, and a sheath 907.

Graft construct 900 may include a component configured to permit spinal fusion of a first spinal segment and a second spinal segment.

Graft construct 900 may include any suitable dimensions for permitting spinal fusion of a first spinal segment and a second spinal segment. Additionally, graft construct 900 may include any suitable material for permitting spinal fusion of a first spinal segment and a second spinal segment. Graft construct 900 may include an allograft, an autograft, an isograft, a xenograft, a composite graft, a synthetic graft, and/or the like.

Graft construct 900 may include a synthetic, polylactic acid, polyglyconate, calcium sulfate, calcium phosphate, a calcium-based synthetic, a hydroxylapatite-based synthetic, polylactic-co-glycolic acid (PLGA), thiolactic acid (TLA), and/or the like.

Lower graft portion 905 and upper graft portion 906 may include the same dimensions, the same materials, the same type of graft, and/or the like. Alternatively, lower graft portion 905 and upper graft portion 906 may include different dimensions, different materials, different types of grafts, and/or the like.

Suture 800 may enter graft construct 900 via first connection mechanism 903, longitudinally extend through graft construct 900, and exit graft construct 900 via second connection mechanism 904. In this way, suture 800 may be connected to first anchor assembly 401 at first end 901 of graft construct 900, and may be connected to second anchor assembly 402 at second end 902 of graft construct 900.

Alternatively, multiple sutures 800 may be used to connect first anchor assembly 401, graft construct 900, and/or second anchor assembly 402. For example, a first suture 800 may connect first anchor assembly 401 and graft construct 900 at first end 901 of graft construct 900, and a second suture 800 may connect second anchor assembly 402 and graft construct 900 at second end 902 of graft construct 900. Additionally, or alternatively, suture(s) 800 may connect to graft construct 900 via first connection mechanism 903 and/or second connection mechanism 904. It should be understood that many types of configurations are possible regarding connecting graft construct 900 to first anchor assembly 401 and/or second anchor assembly 402.

The number and arrangement of components shown in FIGS. 1-9 are provided as an example. In practice, there may be additional components, fewer components, different components, or differently arranged components than those shown in FIGS. 1-9. Furthermore, two or more components shown in FIGS. 1-9 may be implemented within a single component, or a single component shown in FIGS. 1-9 may be implemented as multiple, distributed components. Additionally, or alternatively, a set of components (e.g., one or more components) may perform one or more functions described as being performed by another set of components.

Figure 10:
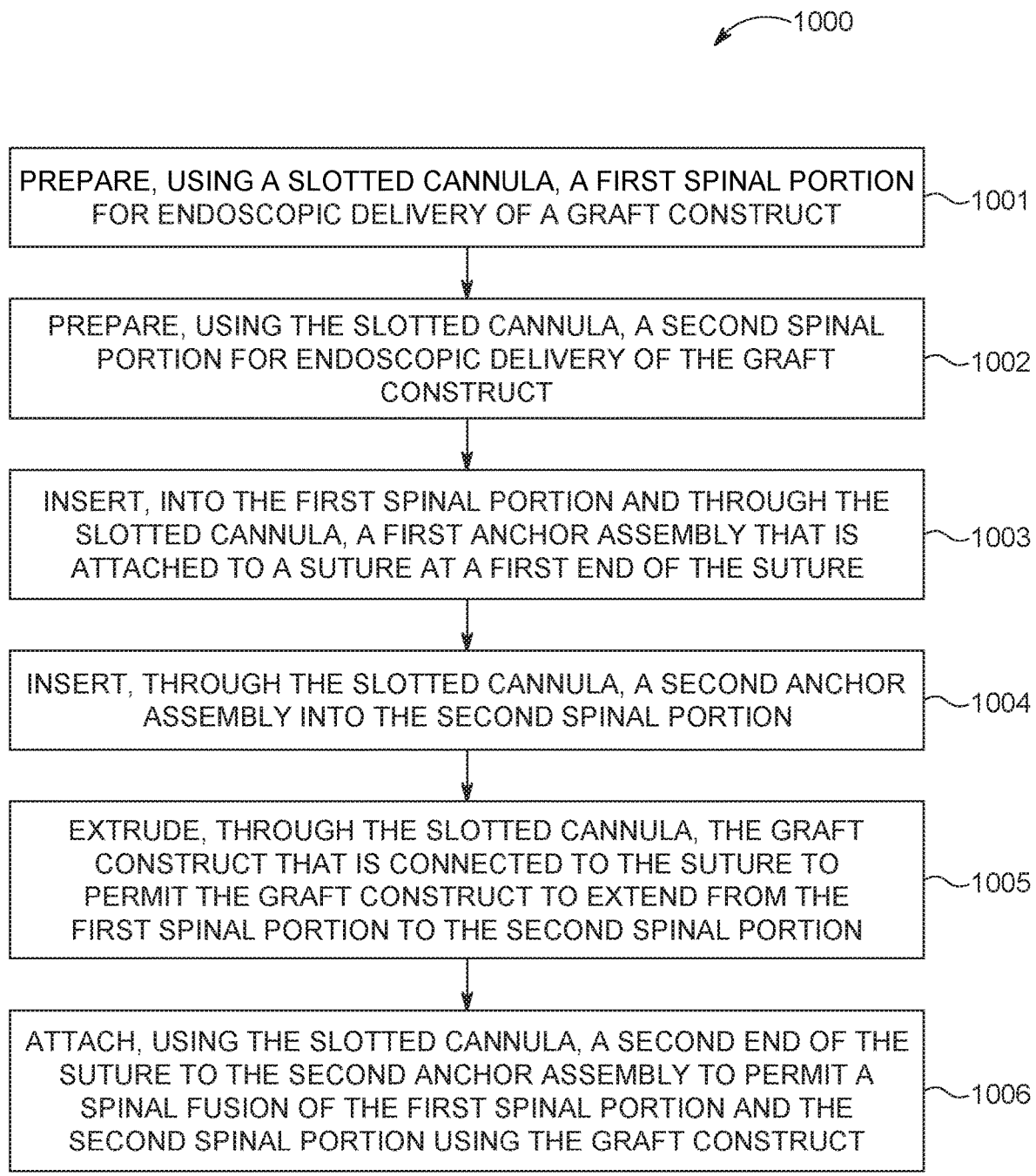
FIG. 10 is a flowchart of an example process for performing endoscopic graft delivery using a slotted cannula.

FIG. 10 is a flowchart of a flowchart of an example process 1000 for performing endoscopic graft delivery using slotted cannula 100.

As shown in FIG. 10, process 1000 may include preparing, using a slotted cannula, a first spinal segment for endoscopic delivery of a graft construct (block 1001). For example, a surgeon may prepare, using slotted cannula 100, a first spinal segment, of a patient, for endoscopic delivery of graft construct 900 to permit spinal fusion of the first spinal segment and a second spinal segment.

Figure 11:
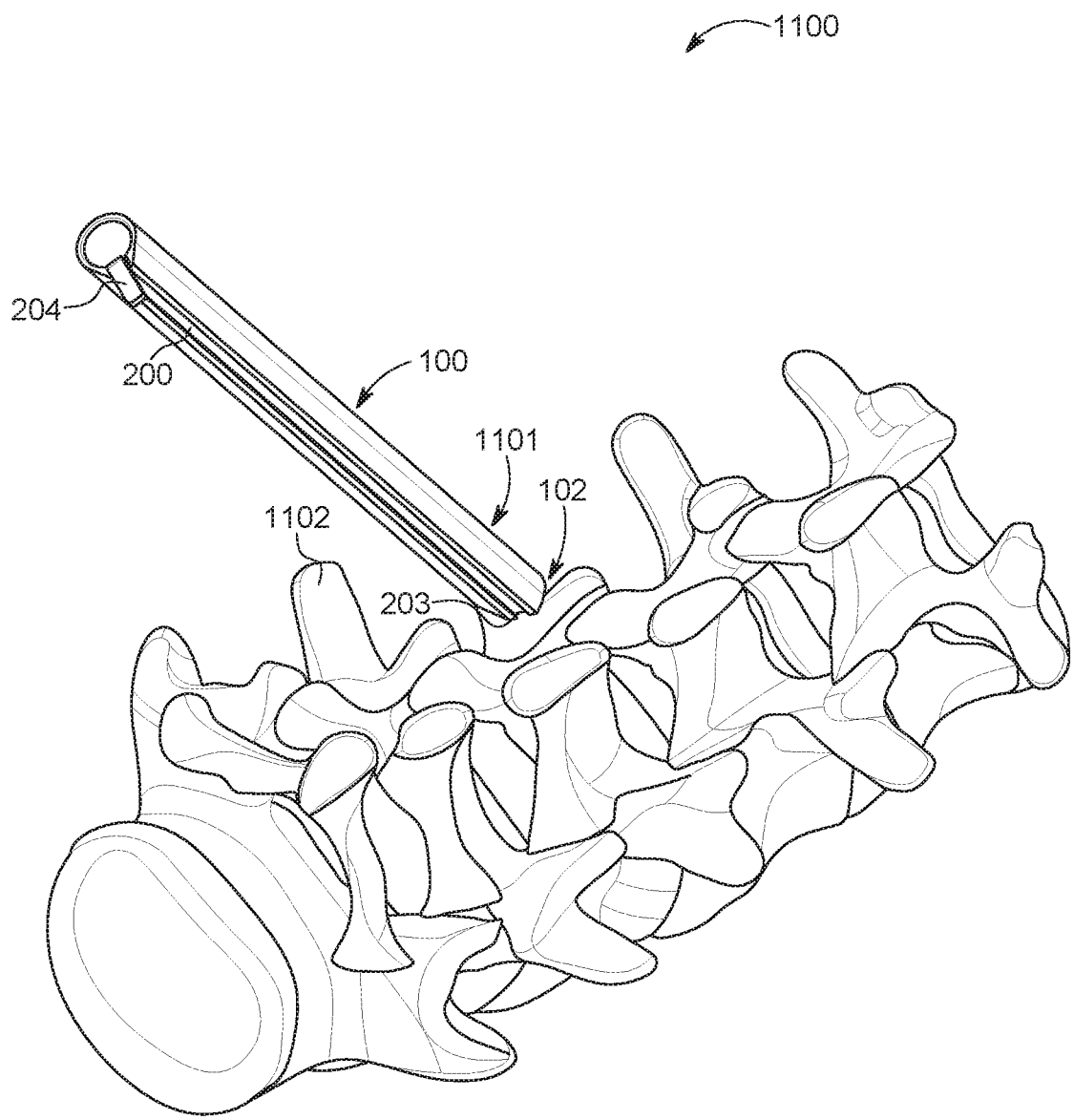
FIG. 11 is an isometric view of a section of vertebrae with a slotted cannula accessing a first spinal segment.

As shown in FIG. 11, a section 1100 of vertebrae may include a first spinal segment 1101, and a second spinal segment 1102. First spinal segment 1101 may be associated with a first vertebra, and second spinal segment 1102 may be associated with a second vertebra. Additionally, or alternatively, first spinal segment 1101 may include a first transverse process (e.g., a superior transverse process) of a first vertebra, and second spinal segment 1102 may include a second transverse process (e.g., an inferior transverse process) of a second vertebra. The first vertebra and the second vertebra may be cervical vertebrae, thoracic vertebrae, lumbar vertebrae, and/or sacral vertebrae.

The surgeon may create an incision to permit slotted cannula 100 to be inserted into the patient and access first spinal segment 1101 of the patient. Additionally, or alternatively, the surgeon may insert distal end 102 of slotted cannula 100 through the incision and into the patient to permit distal end 102 of slotted cannula 100 to access first spinal segment 1101 of the patient.

The incision may include a set of dimensions that is substantially non-invasive in nature. For example, the incision may include a diameter that is substantially the same as an outer diameter of slotted cannula 100. Alternatively, the incision may be smaller than an outer diameter of slotted cannula 100. In this way, the procedure may be performed more safely, with less deleterious effects, with less pain, etc. than as compared to situations where a larger incision is made or situations where multiple incisions are made.

A first spinal segment 1101 is prepared for insertion of first anchor assembly 401 in the following manner. For example, as shown in FIG. 11, distal end 102 of slotted cannula 100 may access first spinal segment 1101 of the patient such that distal end 102 of slotted cannula 100 is substantially flush with first spinal segment 1101. Slotted cannula 100 may include blade 200 while slotted cannula 100 is inserted into the patient. In other words, blade 200 may be disposed within longitudinal channel 104 of slotted cannula 100 while slotted cannula 100 is inserted into the patient through the incision.

The surgeon may insert tip 203 of blade 200 into first spinal segment 1101, based on slotted cannula 100 accessing first spinal segment 1101, to permit slotted cannula 100 to be anchored with respect to first spinal segment 1101. For example, the surgeon may manipulate tab 204 of blade 200 to cause tip 203 of blade 200 to be inserted into first spinal segment 1101.

The surgeon may drill a pilot hole into first spinal segment 1101 based on inserting slotted cannula 100 into the patient. For example, the surgeon may insert a drilling tool into cavity 105 of slotted cannula 100, and drill a pilot hole in first spinal segment 1101 using the drilling tool.

Figure 12:
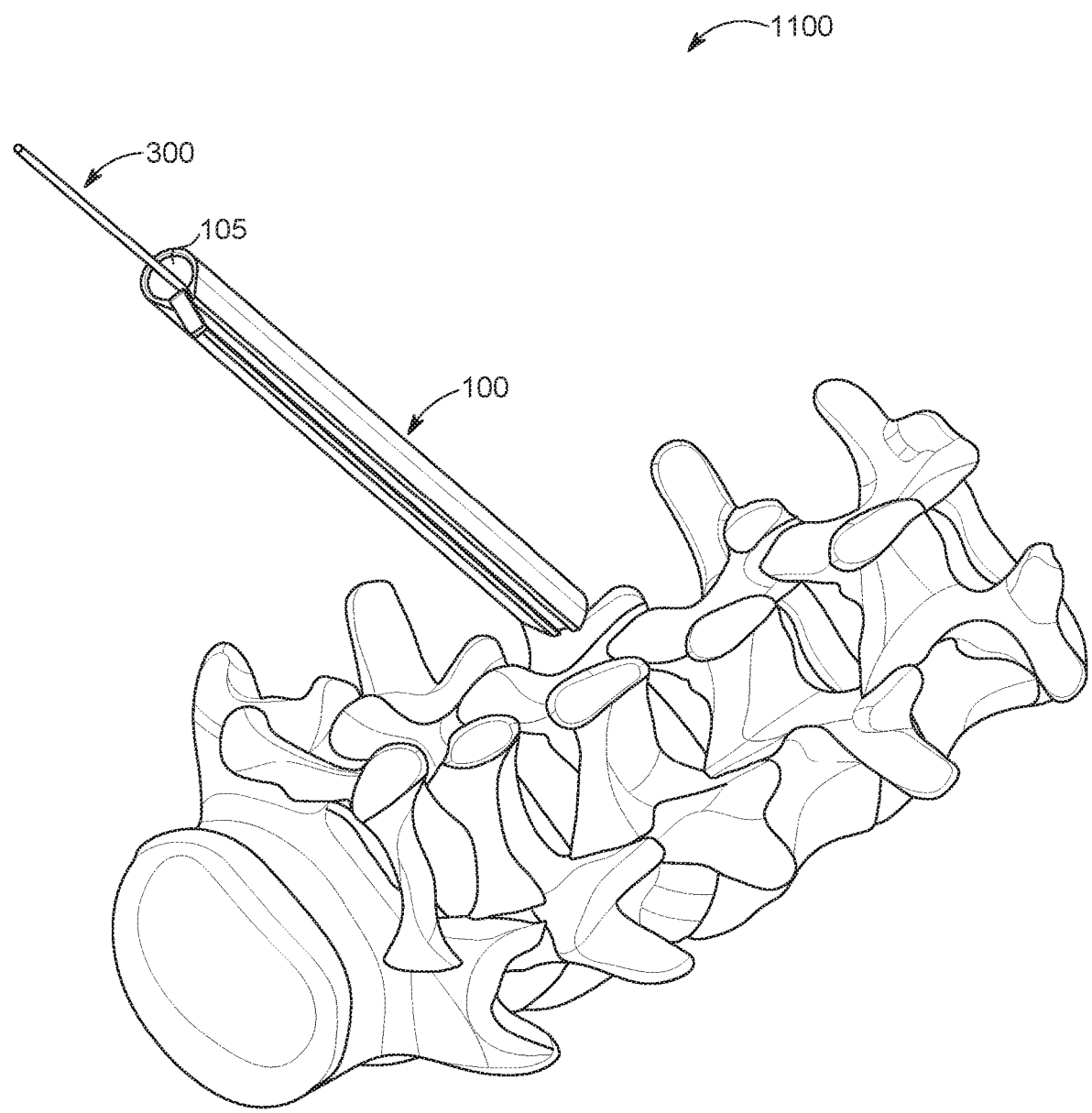
FIG. 12 is an isometric view of the section of vertebrae with a guidewire inserted into the slotted cannula.

The surgeon may insert distal end 302 of guidewire 300 into cavity 105 of slotted cannula 100 based on drilling the pilot hole. Additionally, or alternatively, the surgeon may insert tip 303 of guidewire 300 into the pilot hole of first spinal segment 1101. For example, as shown in FIG. 12, guidewire 300 may be inserted into cavity 105 of slotted cannula 100.

The surgeon may drill a hole in first spinal segment 1101 based on inserting guidewire 300 into cavity 105 of slotted cannula 100. For example, the surgeon may, using guidewire 300 as a guide, insert a drilling tool into cavity 105 of slotted cannula 100 and drill a hole in first spinal segment 1101. In this way, the surgeon may prepare first spinal segment 1101 for insertion of first anchor assembly 401, as described elsewhere herein.

Figure 13A:
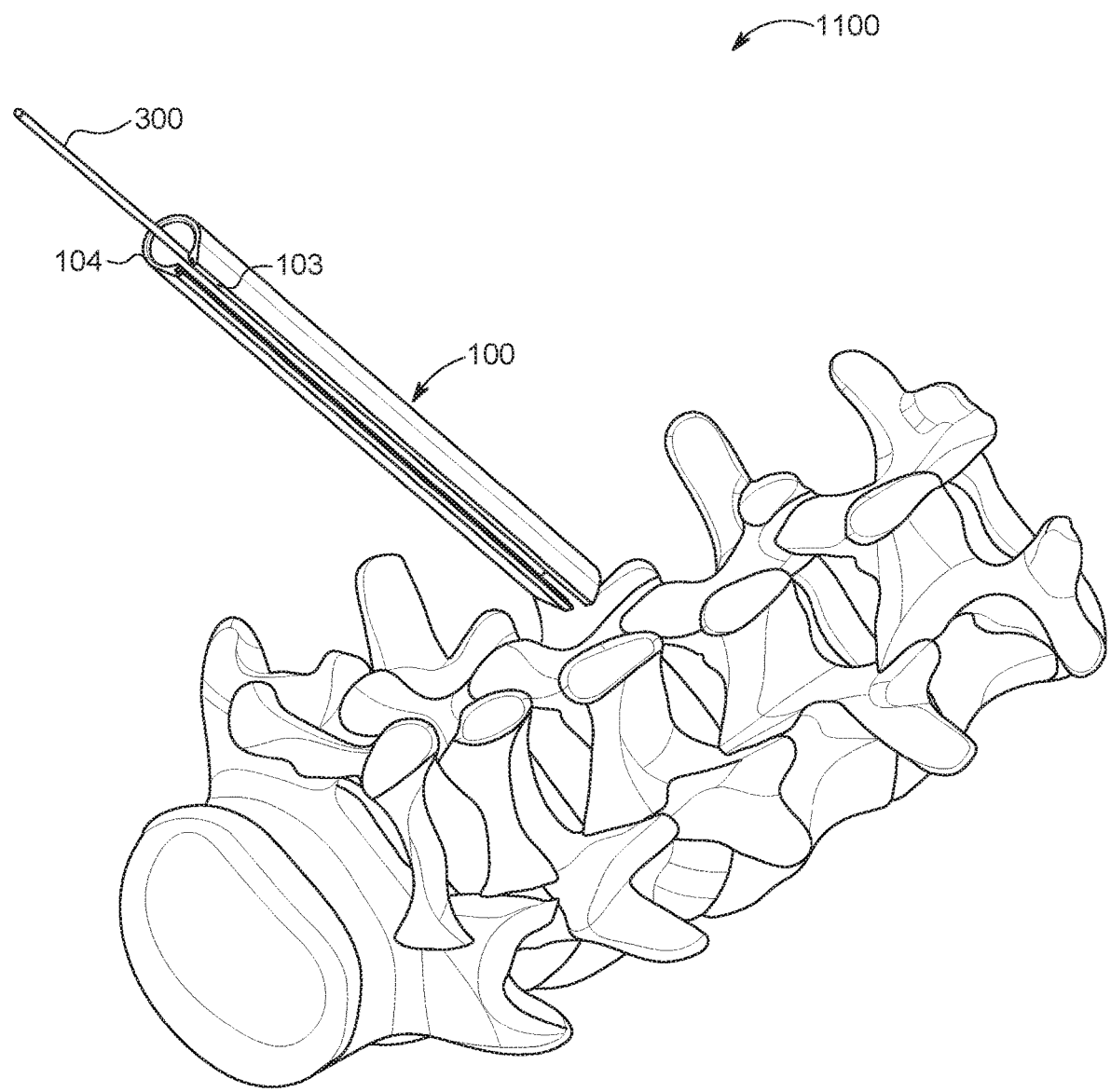
FIG. 13A is an isometric view of the section of vertebrae with a blade removed from the slotted cannula.
Figure 13B:
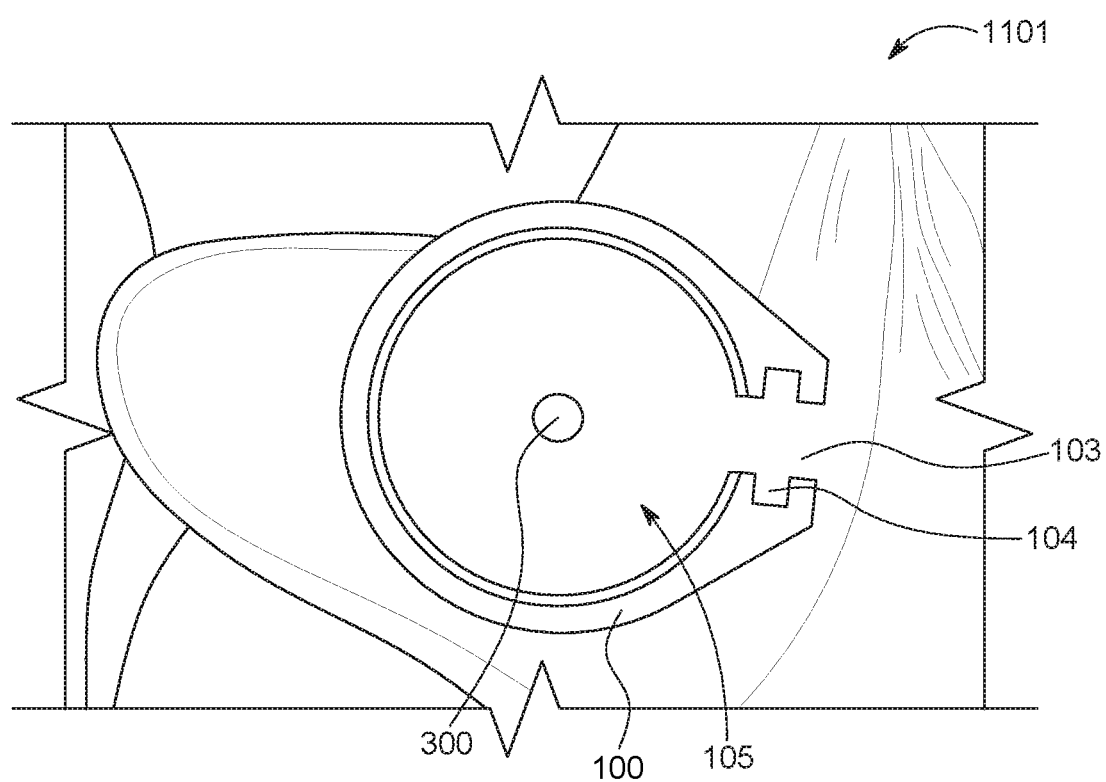
FIG. 13B is a top view of the first spinal segment, the slotted cannula, and the guidewire.

The surgeon may remove blade 200 from longitudinal channel 104 of slotted cannula 100 based on inserting guidewire 300 into the pilot hole and/or drilling the hole in first spinal segment 1101. For example, as shown in FIG. 13A, blade 200 may be removed from longitudinal channel 104 of slotted cannula 100, thereby exposing longitudinal slot 103 of slotted cannula 100. Additionally, as shown in FIG. 13B, guidewire 300 may be disposed within cavity 105 of slotted cannula 100 while slotted cannula 100 is accessing first spinal segment 1101.

Figure 14A:
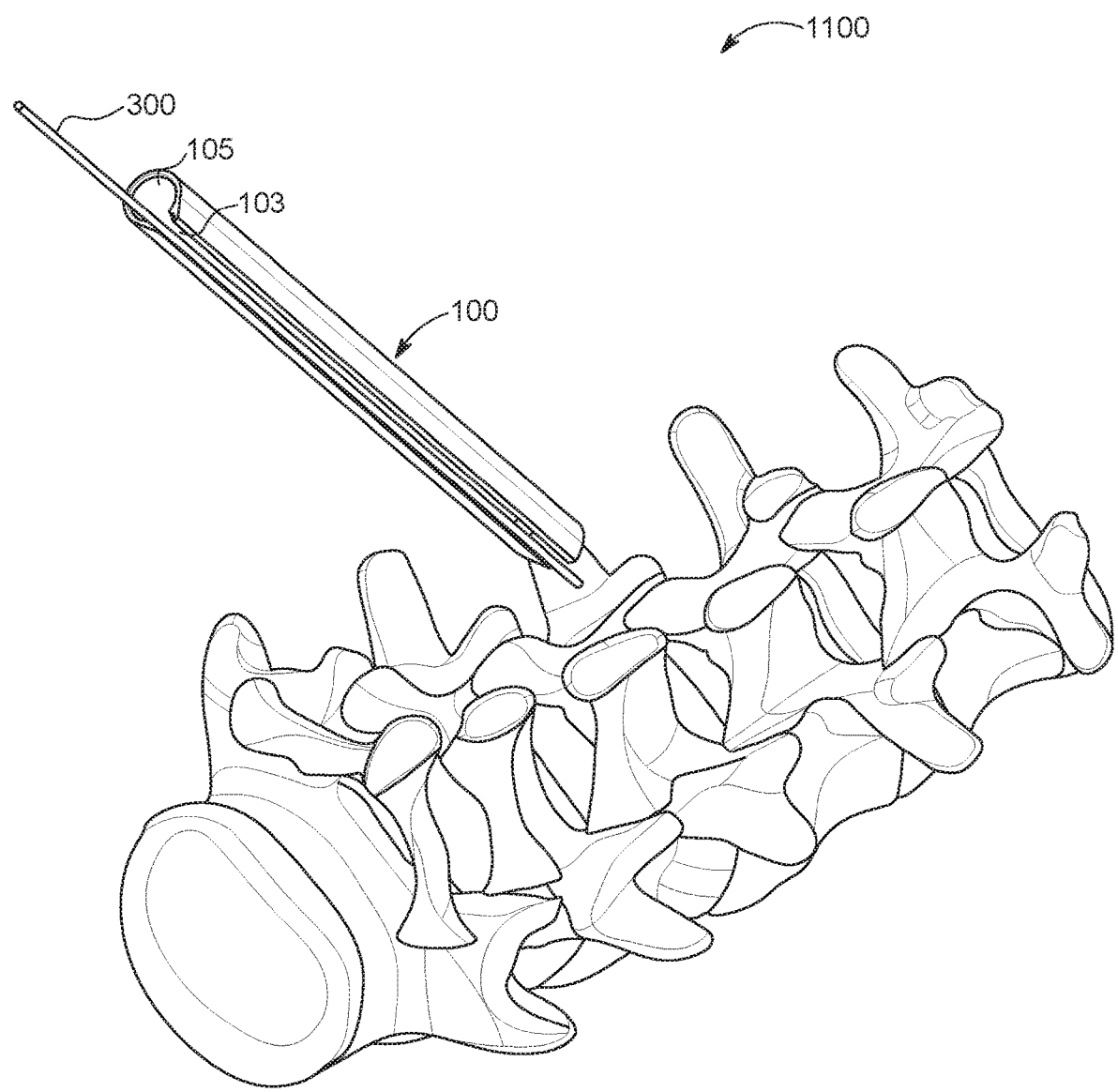
FIG. 14A is an isometric view of the section of vertebrae with the slotted cannula being translated with respect to the guidewire.

The surgeon may translate slotted cannula 100 with respect to guidewire 300. For example, as shown in FIG. 14A, slotted cannula 100 may be translated with respect to guidewire 300 such that guidewire 300 is no longer disposed within slotted cannula 100. Longitudinal slot 103 of slotted cannula 100 may permit guidewire 300 to be translated through slotted cannula 100 such that guidewire 300 is no longer disposed within cavity 105 of slotted cannula 100. For example, as shown in FIG. 14B, guidewire 300 may translate through longitudinal slot 103 of slotted cannula 100 such that guidewire 300 is no longer disposed within cavity 105 of slotted cannula 100.

It should be understood that guidewire 300 may remain stationary while slotted cannula 100 is translated with respect to guidewire 300. In other words, guidewire 300 may remain stationary as guidewire 300 is translated through longitudinal slot 103 of slotted cannula 100.

Figure 14B:
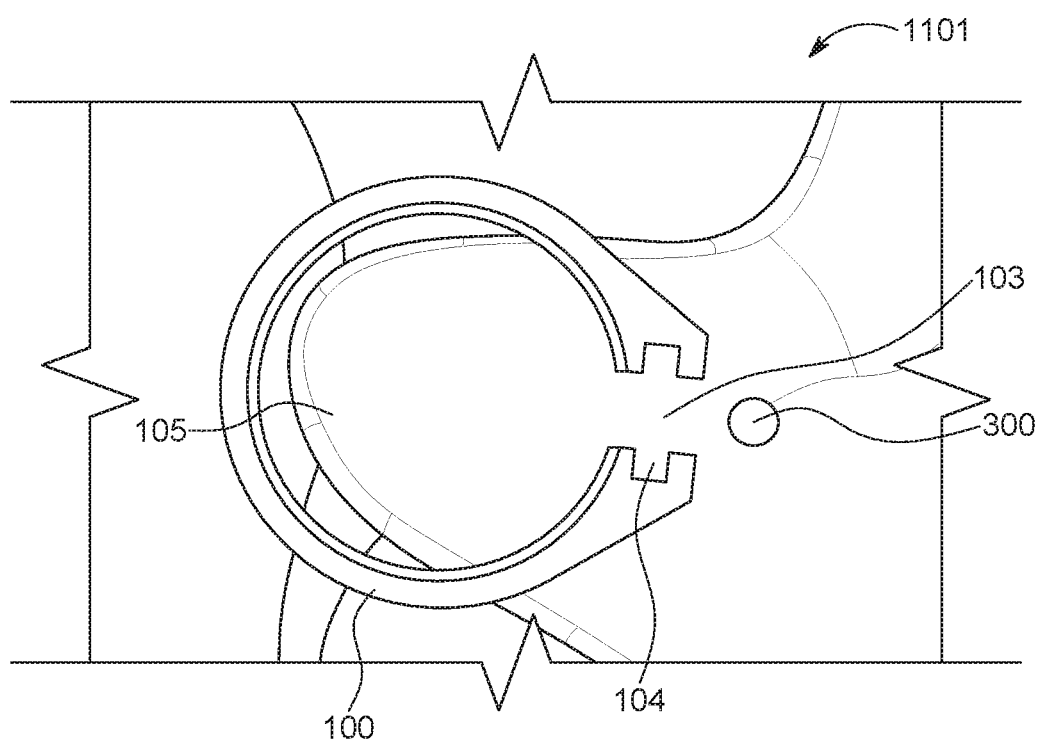
FIG. 14B is a top view of the first spinal segment with the slotted cannula being translated with respect to the guidewire.

The surgeon may, using a drilling tool and slotted cannula 100, decorticate areas of the first spinal segment 1101 by moving slotted cannula 100 along a surface of first spinal segment 1101, as shown in FIG. 14A and FIG. 14B, and using the drilling tool to decorticate areas of the first spinal segment 1101. For example, the surgeon may decorticate areas of first spinal segment 1101 to allow progenitor cells to access the areas of first spinal segment 1101 and/or promote angiogenesis. By permitting guidewire 300 to be translated through longitudinal slot 103 of slotted cannula 100, some implementations herein reduce a need of the surgeon to remove slotted cannula 100 through the incision and/or over guidewire 300. In this way, some implementations herein improve speed, accuracy, and/or efficacy of graft delivery, and/or reduce a risk of complications.

Figure 15A:
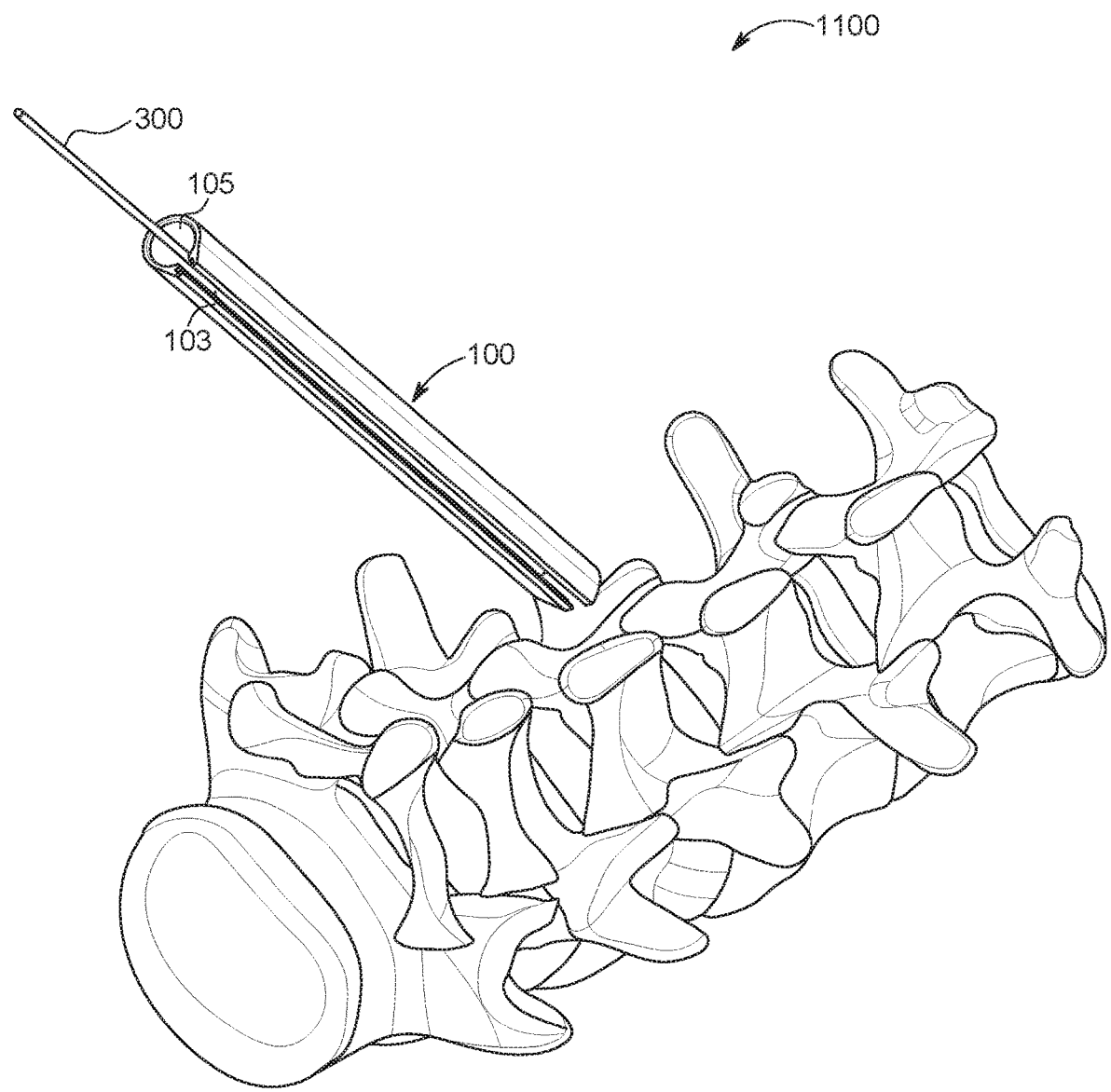
FIG. 15A is an isometric view of the section of vertebrae with the slotted cannula being untranslated with respect to the guidewire.
Figure 15B:
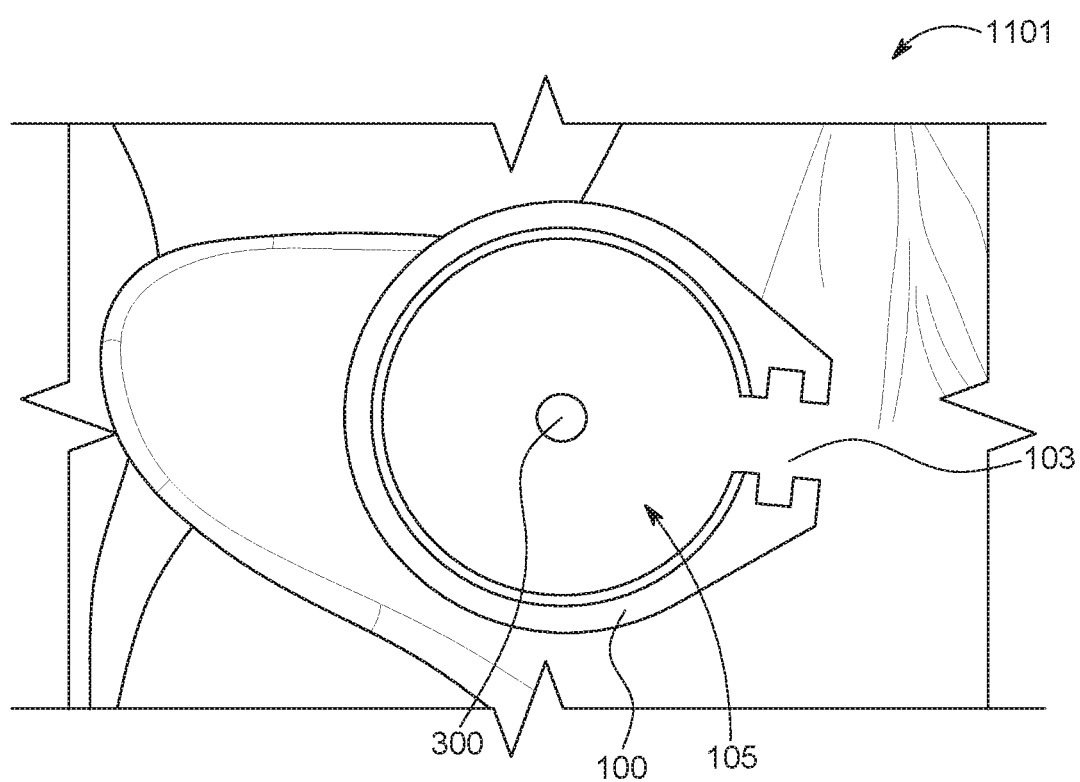
FIG. 15B is a top view of the first spinal segment with the slotted cannula being untranslated with respect to the guidewire.

The surgeon may translate slotted cannula 100, such that slotted cannula 100 is moved back to the position shown in FIGS. 13A and 13B, and guidewire 300 is disposed within cavity 105 of slotted cannula 100, based on decorticating the areas of first spinal segment 1101. For example, as shown in FIGS. 15A and 15B, guidewire 300 may be translated through longitudinal slot 103 of slotted cannula 100 such that guidewire 300 is disposed within cavity 105 of slotted cannula 100 and returned to the position shown in FIG. 13A and FIG. 13B.

Figure 16A:
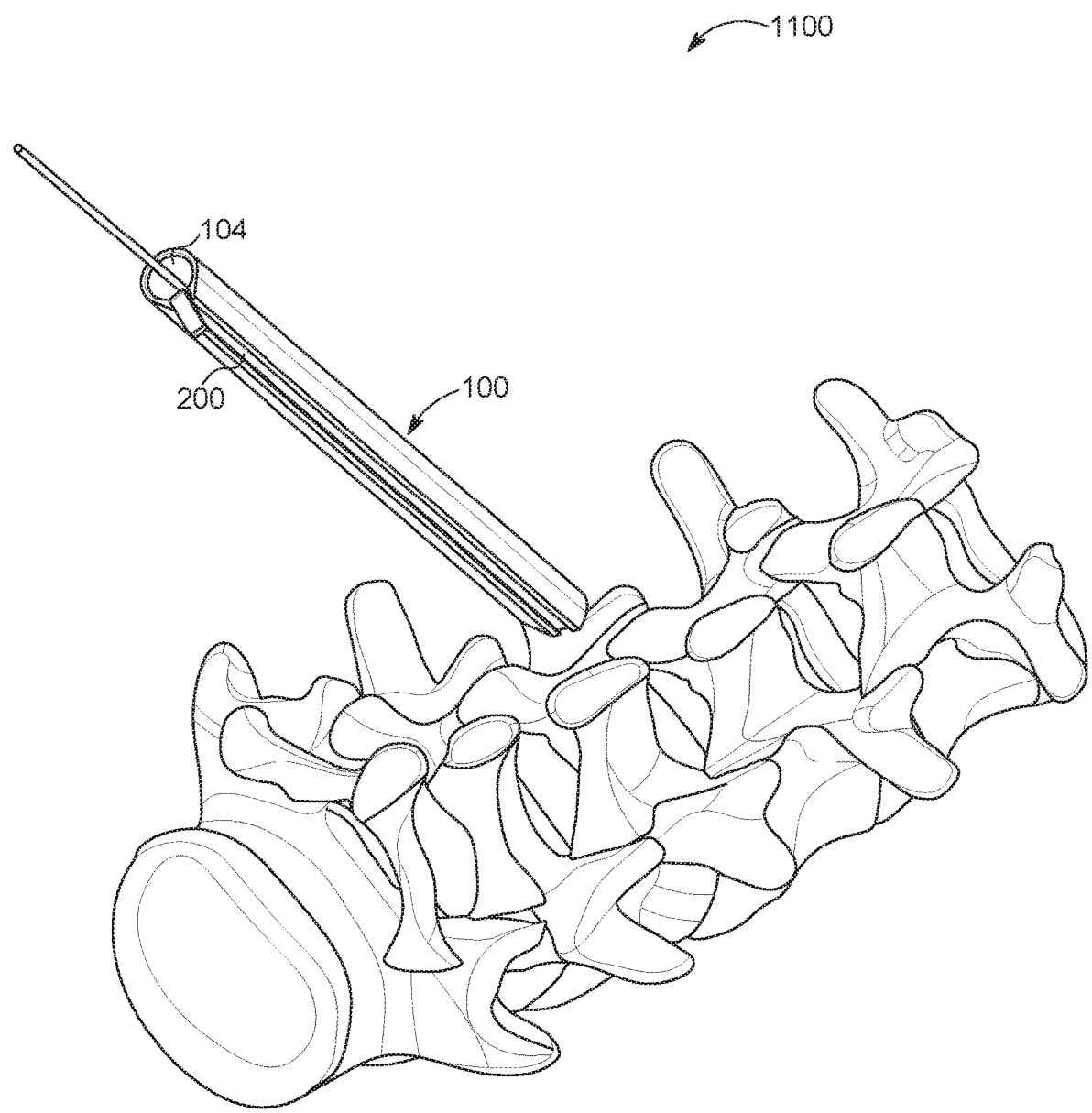
FIG. 16A is an isometric view of the section of vertebrae with the blade inserted into the slotted cannula.
Figure 16B:
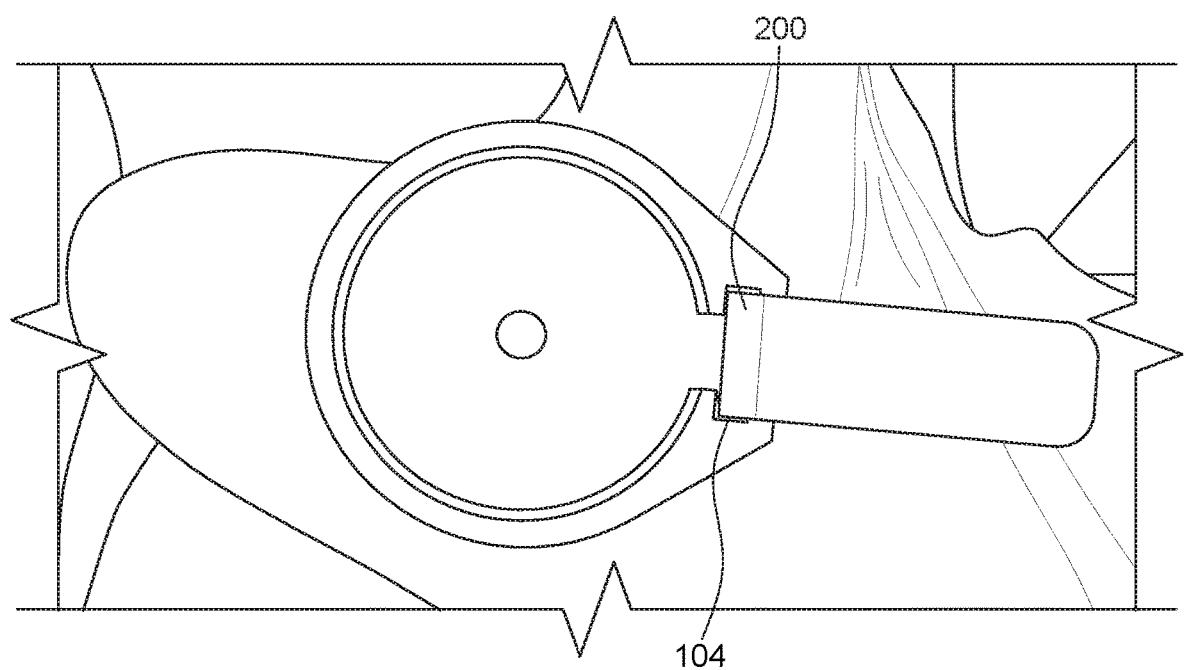
FIG. 16B is a top view of the first spinal segment with the blade inserted into the slotted cannula.

The surgeon may insert blade 200 into longitudinal channel 104 of slotted cannula 100 based on guidewire 300 being disposed within cavity 105 of slotted cannula 100. For example, as shown in FIGS. 16A and 16B, blade 200 may be inserted into longitudinal channel 104 of slotted cannula 100.

The surgeon may manipulate tab 204 of blade 200 to cause tip 203 of blade 200 to be inserted into first spinal segment 1101. In this way, slotted cannula 100 may be anchored with respect to first spinal segment 1101. Additionally, in this way, the surgeon may insert first anchor assembly 401 into the hole associated with first spinal segment 1101, as described elsewhere herein.

As further shown in FIG. 10, process 1000 may include preparing, using the slotted cannula, a second spinal segment for endoscopic delivery of the graft construct (block 1002). For example, the surgeon may prepare, using slotted cannula 100, second spinal segment 1102 for endoscopic delivery of graft construct 900.

The surgeon may prepare second spinal segment 1102 in a substantially similar manner as described above in connection with block 1001. The surgeon may translate slotted cannula 100 to second spinal segment 1102, and perform similar operations as described above in connection with block 1001. In this way, the surgeon may prepare second spinal segment 1102 for insertion of second anchor assembly 402, as described elsewhere herein. Additionally, the surgeon may translate slotted cannula 100 back to first spinal segment 1101 to permit the surgeon to insert first anchor assembly 401 into first spinal segment 1101, as described below.

As further shown in FIG. 10, process 1000 may include inserting, into the first spinal segment and through the slotted cannula, a first anchor assembly that is attached to a suture at a first end of the suture (block 1003). For example, the surgeon may insert, into first spinal segment 1101 and through slotted cannula 100, first anchor assembly 401 that is attached to suture 800 at a first end of suture 800.

The surgeon may attach first anchor assembly 401 to anchor driver 500. For example, the surgeon may mate tip 503 of anchor driver 500 with head portion 404 of first anchor assembly 401.

The surgeon may place first anchor assembly 401 over guidewire 300 that is disposed within cavity 105 of slotted cannula 100. For example, the surgeon may insert anchor portion 403 over proximal end 301 of guidewire 300 to permit first anchor assembly 401 to be translated towards the hole of first spinal segment 1101 using guidewire 300 as a guide.

The surgeon may, using anchor driver 500, translate first anchor assembly 401 towards the hole of first spinal segment 1101, and insert anchor portion 403 of first anchor assembly 401 into the hole of first spinal segment 1101.

The surgeon may, using anchor driver 500, cause first anchor assembly 401 to be anchored to first spinal segment 1101.

The first anchor assembly 401 may include a connected graft construct 900. For example, first anchor assembly 401 and graft construct 900 may be a unitary construct, may be connected, may be fastened together, and/or the like. As such, first anchor assembly 401 and graft construct 900 may be inserted into slotted cannula 100 substantially simultaneously in such situations.

Figure 17A:
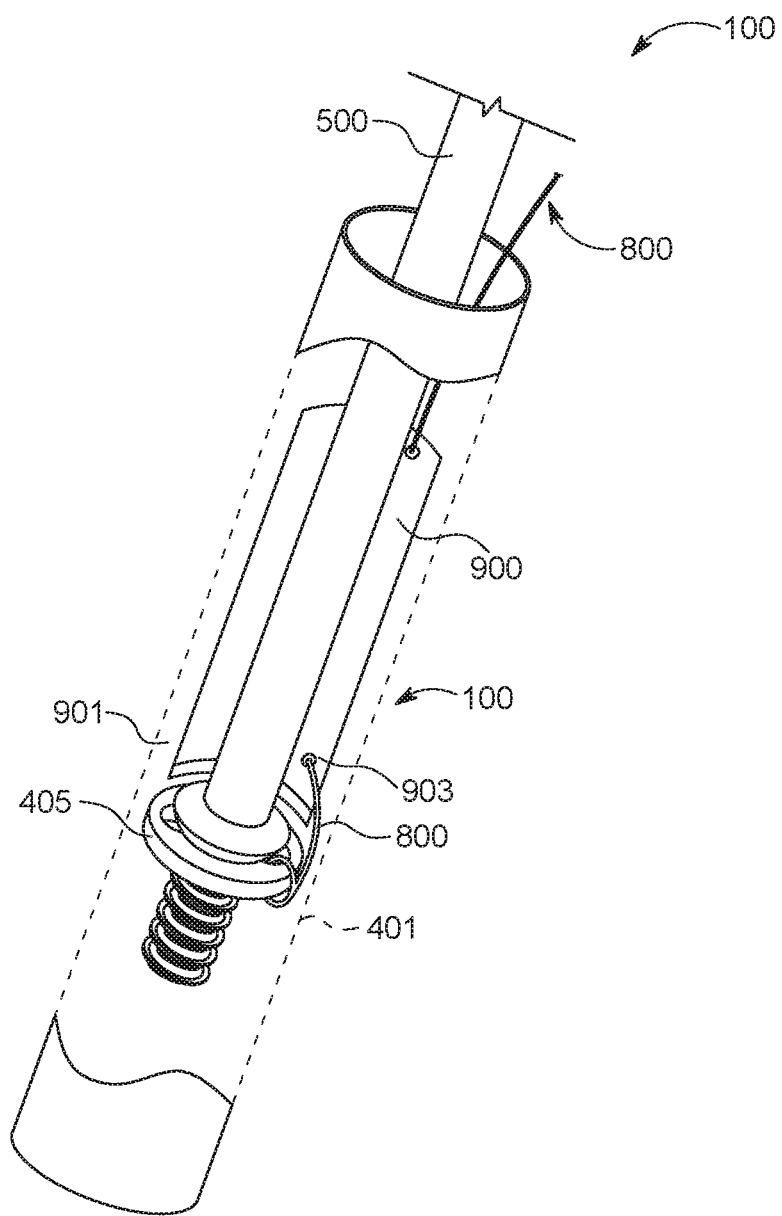
FIG. 17A is a close-up view of a first anchor assembly, including a connected graft construct, inserted into the slotted cannula.

As an example, and as shown in FIG. 17A, first anchor assembly 401 and a connected graft construct 900 may be inserted into slotted cannula 100. Additionally, anchor driver 500 may be inserted into slotted cannula 100 to permit first anchor assembly 401 to be fastened to first spinal segment 1101. As shown in FIG. 17A, washer 405 of first anchor assembly 401 may be connected to first end 901 of graft construct 900 via suture 800. For example, suture 800 may be tied through a hole in washer 405, and connected to first end 901 of graft construct 900 via first connection mechanism 903. In this way, first anchor assembly 401, including connected graft construct 900, may be inserted into slotted cannula 100 substantially simultaneously to permit first anchor assembly 401 to be inserted into first spinal segment 1101, and to alleviate a need of graft construct 900 to be connected to first anchor assembly 401 after first anchor assembly 401 is inserted into first spinal segment 1101. Additionally, as shown, suture 800 may extend towards proximal end 101 of slotted cannula 100, thereby permitting suture tool 700 to manipulate suture 800 to connect to second anchor assembly 402, as described elsewhere herein.

As shown in FIG. 17A, suture 800 may extend through graft construct 800, and out of graft construct 800 through first connection mechanism 903. Additionally, suture 800 may enter through a first hole of washer 405 and wrap around anchor portion 403 under washer 405. Additionally, suture 800 may enter through a second hole (or the first hole) of washer 405 and connect to suture 800. For example, suture 800 may be tied to suture 800. Another end of suture 800 may exit graft construct 900 through second connection mechanism 904, thereby permitting suture tool 700 to manipulate the other end of suture 800. It should be understood that many types of methods for connecting suture 800 to first anchor assembly 401 to permit graft construct 900 to be connected to first anchor assembly 401 are possible. Alternatively, suture 800 may be connected (e.g., tied, attached, etc.) to washer 405 to permit graft construct 900 to connect to first anchor assembly 401.

Figure 17B:
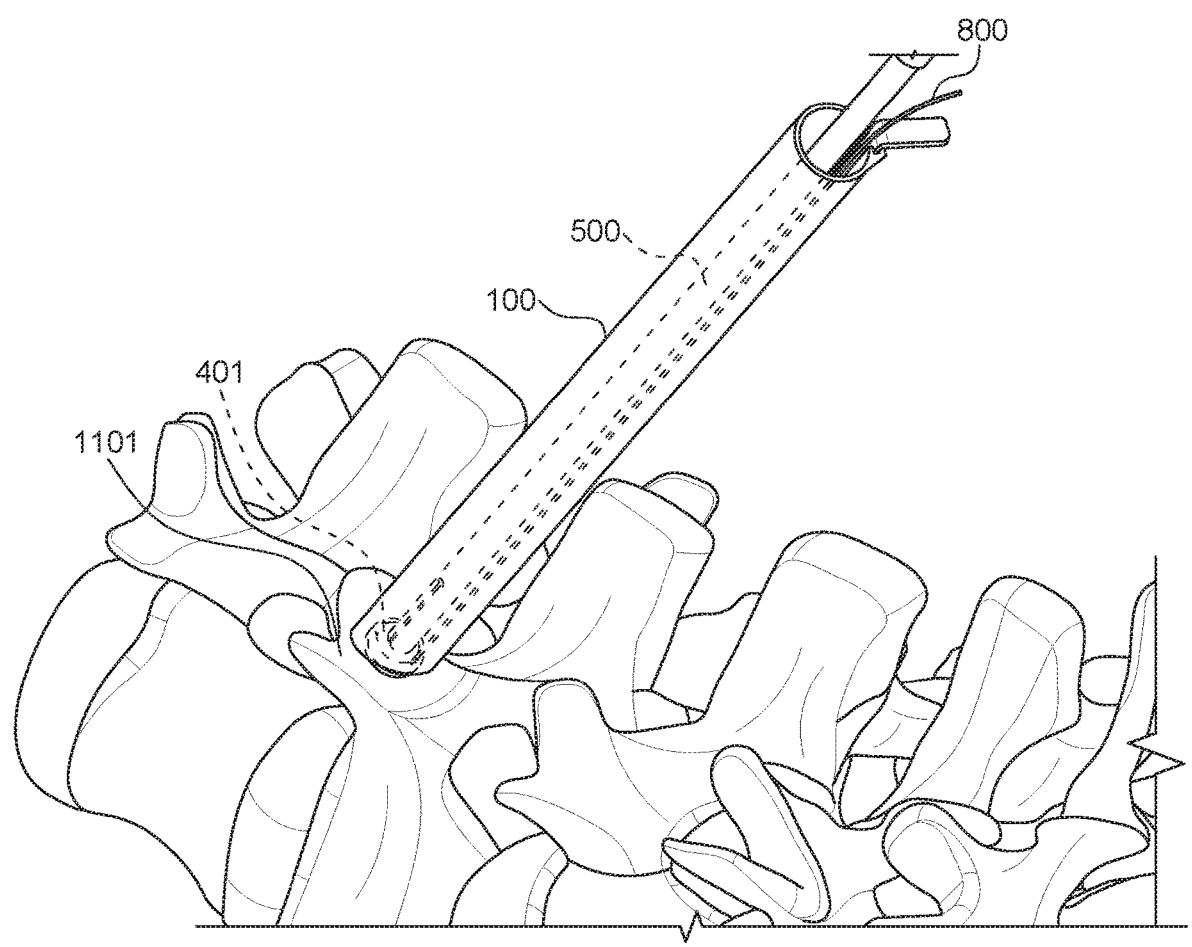
FIG. 17B is an isometric view of the section of vertebrae with a first anchor assembly and an anchor driver inserted into the slotted cannula.

As an alternative, first anchor assembly 401 may be inserted into slotted cannula 100 without being first connected to graft construct 900. For example, as shown in FIG. 17B, first anchor assembly 401 may be anchored into first spinal segment 1101. In this way, the surgeon may later connect graft construct 900 to first anchor assembly 401, as described below in connection with block 1005. It should be understood that the need of the surgeon to connect graft construct 900 to first anchor assembly 401 is alleviated in situations where graft construct 900 is connected to first anchor assembly 401 prior to first anchor assembly 401 being inserted into slotted cannula 100 and/or inserted into first spinal segment 1101.

The surgeon may remove guidewire 300 from cavity 105 of slotted cannula 100 based on causing first anchor assembly 401 to be anchored to first spinal segment 1101.

In this way, the surgeon may prepare first spinal segment 1101 for graft delivery by inserting and fastening first anchor assembly 401.

As further shown in FIG. 10, process 1000 may include inserting, through the slotted cannula, a second anchor assembly into the second spinal segment (block 1004). For example, the surgeon may insert, through cavity 105 of slotted cannula 100, second anchor assembly 402 into second spinal segment 1102.

Figure 18A:
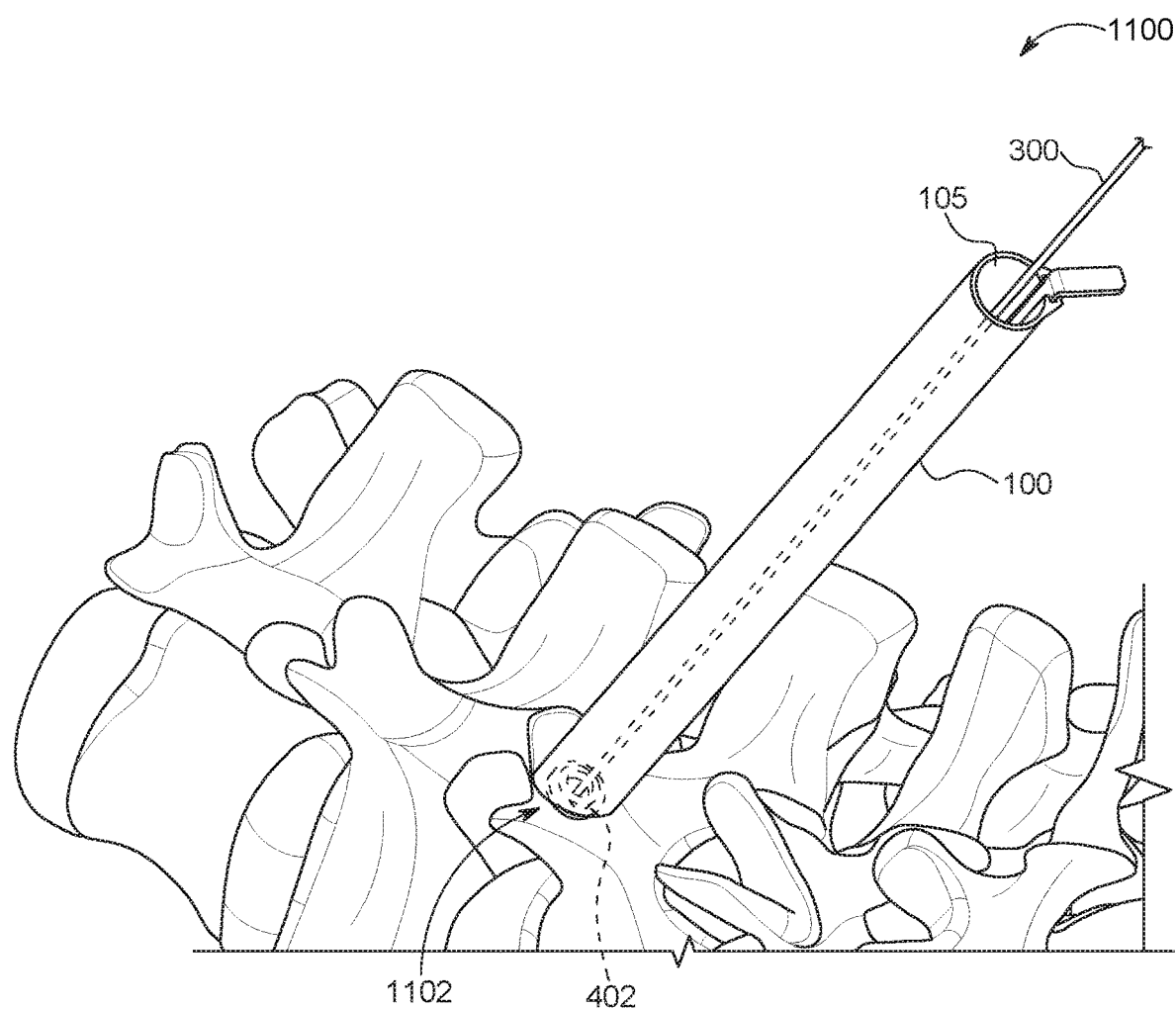
FIG. 18A is an isometric view of the section of vertebrae with a second anchor assembly and a guidewire inserted into the slotted cannula.

The surgeon may insert second anchor assembly 402 into second spinal segment 1102 in a substantially similar manner as described above in connection with block 1002. For example, as shown in FIG. 18A, second anchor assembly 402 may be inserted into second spinal segment 1102 through cavity 105 of slotted cannula 100 and over another guidewire 300.

Figure 18B:
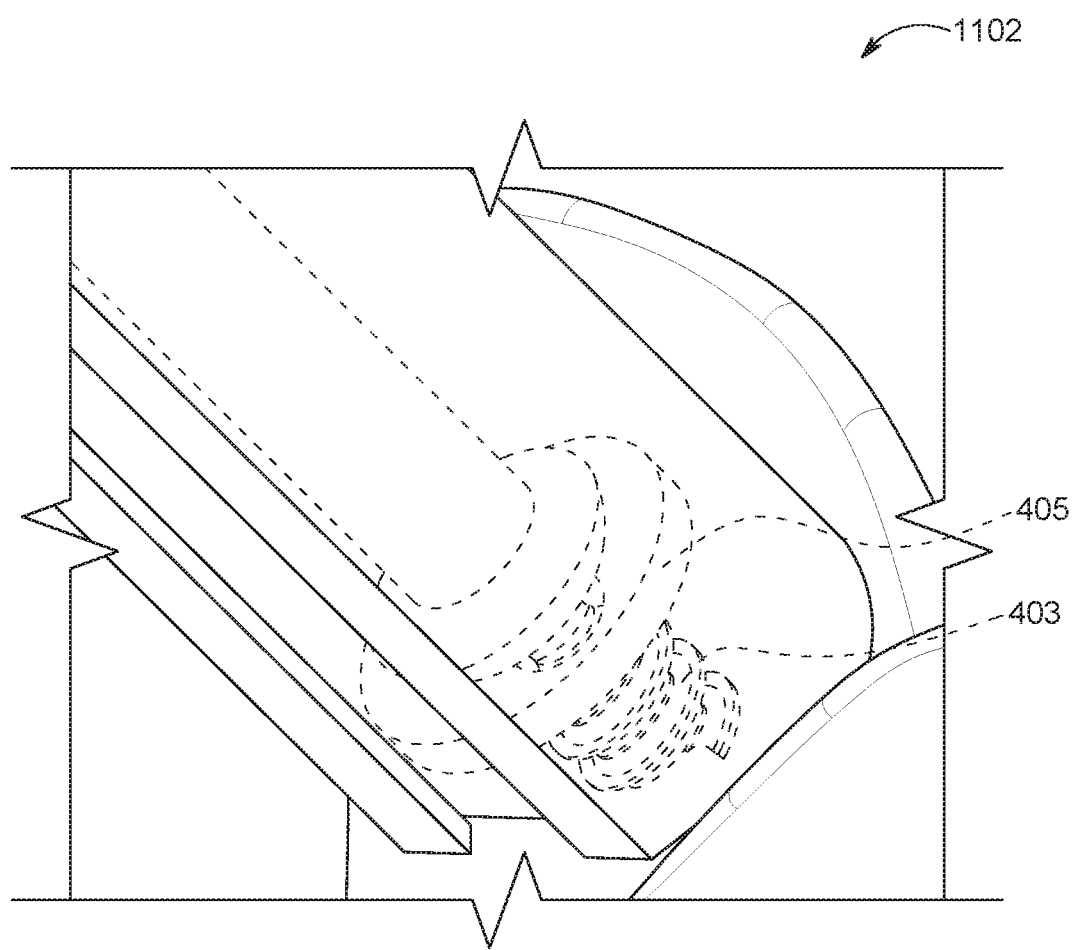
FIG. 18B is a close-up view of the second anchor assembly inserted into a second spinal segment.

The surgeon may cause second anchor assembly 402 to be inserted into second spinal segment 1102 such that a gap exists between a surface of second spinal segment 1102 and a bottom of washer 405 of second anchor assembly 402. For example, as shown in FIG. 18B, washer 405 may be disposed at a threshold distance from a surface of second spinal segment 1102. In this way, the surgeon may wrap suture 800 around anchor portion 403 and under washer 405 of second anchor assembly 402, as described elsewhere herein.

In this way, the surgeon may prepare both first spinal segment 1101 and second spinal segment 1102 for delivery of graft construct 900, and deliver graft construct 900 via slotted cannula 100, as described below.

As further shown in FIG. 10, process 1000 may include extruding, through the slotted cannula, the graft construct that is connected to the suture to permit the graft construct to extend from the first spinal segment to the second spinal segment (block 1005). For example, the surgeon may extrude, through cavity 105 of slotted cannula 100, graft construct 900 to permit graft construct 900 to extend from first spinal segment 1101 to second spinal segment 1102.

The surgeon may translate slotted cannula 100 such that slotted cannula 100 is accessing first spinal segment 1101. Additionally, the surgeon may translate slotted cannula 100 such that slotted cannula 100 is flush with first anchor assembly 401.

The surgeon may connect graft construct 900 to suture 800. For example, the surgeon may thread suture 800 through first connection mechanism 903 and/or second connection mechanism 904 of graft construct 900. As described above, the need of the surgeon to connect graft construct 900 to first anchor assembly 401 is alleviated in situations where graft construct 900 is connected to first anchor assembly 401 prior to first anchor assembly 401 being inserted into slotted cannula 100, and/or in situations where graft construct 900 and first anchor assembly 401 are a unitary construct.

The surgeon may insert first end 901 of graft construct into cavity 105 of slotted cannula 100 based on connecting graft construct 900 to suture 800. Additionally, the surgeon may insert graft construct 900 into cavity 105 of slotted cannula 100 such that graft construct 900 is disposed within cavity 105 of slotted cannula 100.

The surgeon may connect a second end of suture 800 to suture tool 700. For example, the surgeon may thread suture 800 through proximal connection mechanism 704 and/or distal connection mechanism 705 of suture tool 700.

The surgeon may insert suture tool 700 into graft pusher 600. For example, the surgeon may insert distal end 702 of suture tool 700 into cavity 603 of graft pusher 600, and translate longitudinal portion 703 of suture tool 700 through graft pusher 600.

The surgeon may insert graft pusher 600 and suture tool 700 into cavity 105 of slotted cannula 100. For example, the surgeon may insert distal end 602 of graft pusher 600 and distal end 702 of suture tool 700 into cavity 105 of slotted cannula 100.

Figure 19:
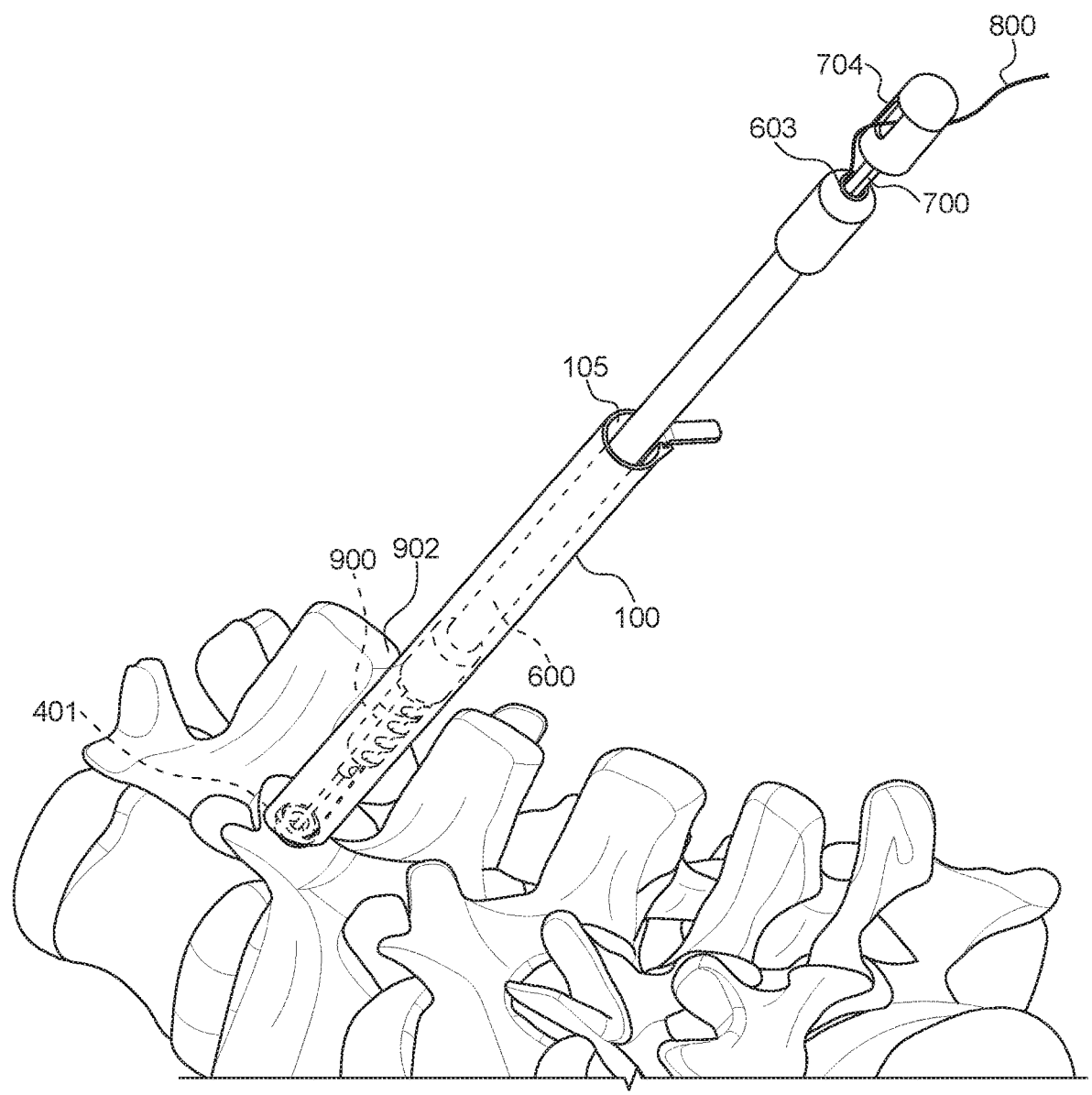
FIG. 19 is an isometric view of the section of vertebrae with a graft construct, a graft pusher, and a suture tool inserted into the slotted cannula.

The surgeon may, using graft pusher 600, translate graft construct 900 towards first anchor assembly 401. For example, as shown in FIG. 19, graft construct 900 may be disposed within cavity 105 of slotted cannula 100 and may be translated towards first anchor assembly 401. Additionally, as further shown in FIG. 19, graft pusher 600 may contact second end 902 of graft construct 900 to cause graft construct 900 to translate towards first anchor assembly 401. Additionally, as further shown in FIG. 19, suture tool 700 may be disposed within cavity 603 of graft pusher 600. Additionally, as further shown in FIG. 19, proximal connection mechanism 704 of suture tool 700 may connect to suture 800.

The surgeon may, using graft pusher 600, translate graft construct 900 such that first end 901 of graft construct 900 is adjacent to first anchor assembly 401. For example, first end 901 of graft construct 900 may include a concave shape that permits first end 901 of graft construct 900 to be disposed substantially adjacent to first anchor assembly 401.

Figure 20A:
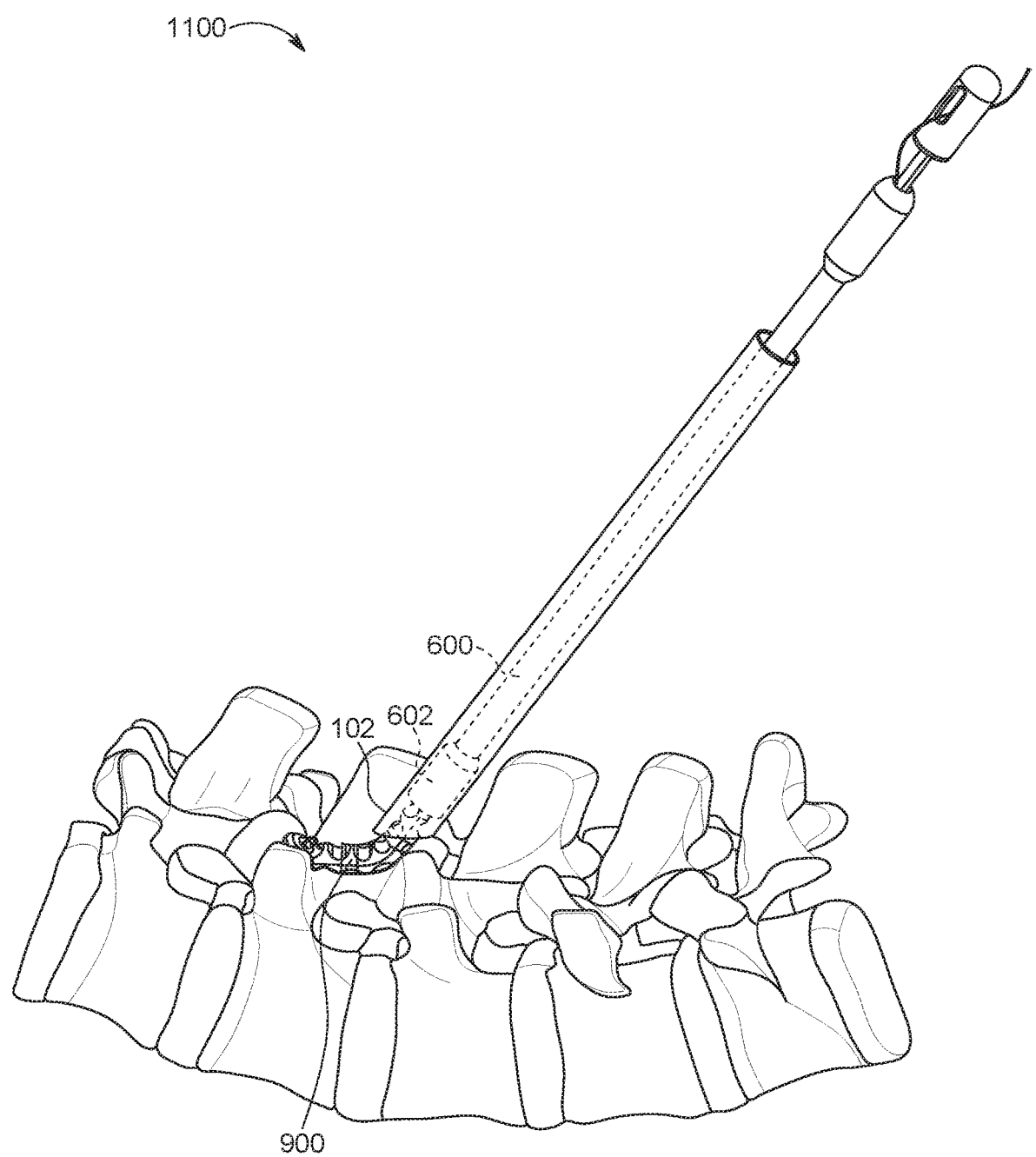
FIG. 20A is an isometric view of the section of vertebrae with the graft construct partially extruded from the slotted cannula.

The surgeon may, using graft pusher 600, extrude graft construct 900 from distal end 102 of slotted cannula 100. For example, the surgeon may manipulate graft pusher 600 to cause graft construct 900 to be extruded from distal end 102 of slotted cannula 100. For example, as shown in FIG. 20A, distal end 602 of graft pusher 600 may translate towards distal end 102 of slotted cannula 100, thereby extruding graft construct 900.

The surgeon may, using graft pusher 600, extrude graft construct 900 from distal end 102 of slotted cannula 100 such that graft construct 900 is no longer disposed within cavity 105 of slotted cannula 100. Additionally, or alternatively, the surgeon may, using graft pusher 600, extrude graft construct 900 such that second end 902 of graft construct 900 is adjacent to second anchor assembly 402. For example, second end 902 may include a concave shape that permits second end 902 of graft construct 900 to be disposed substantially adjacent to second anchor assembly 402.

Figure 20B:
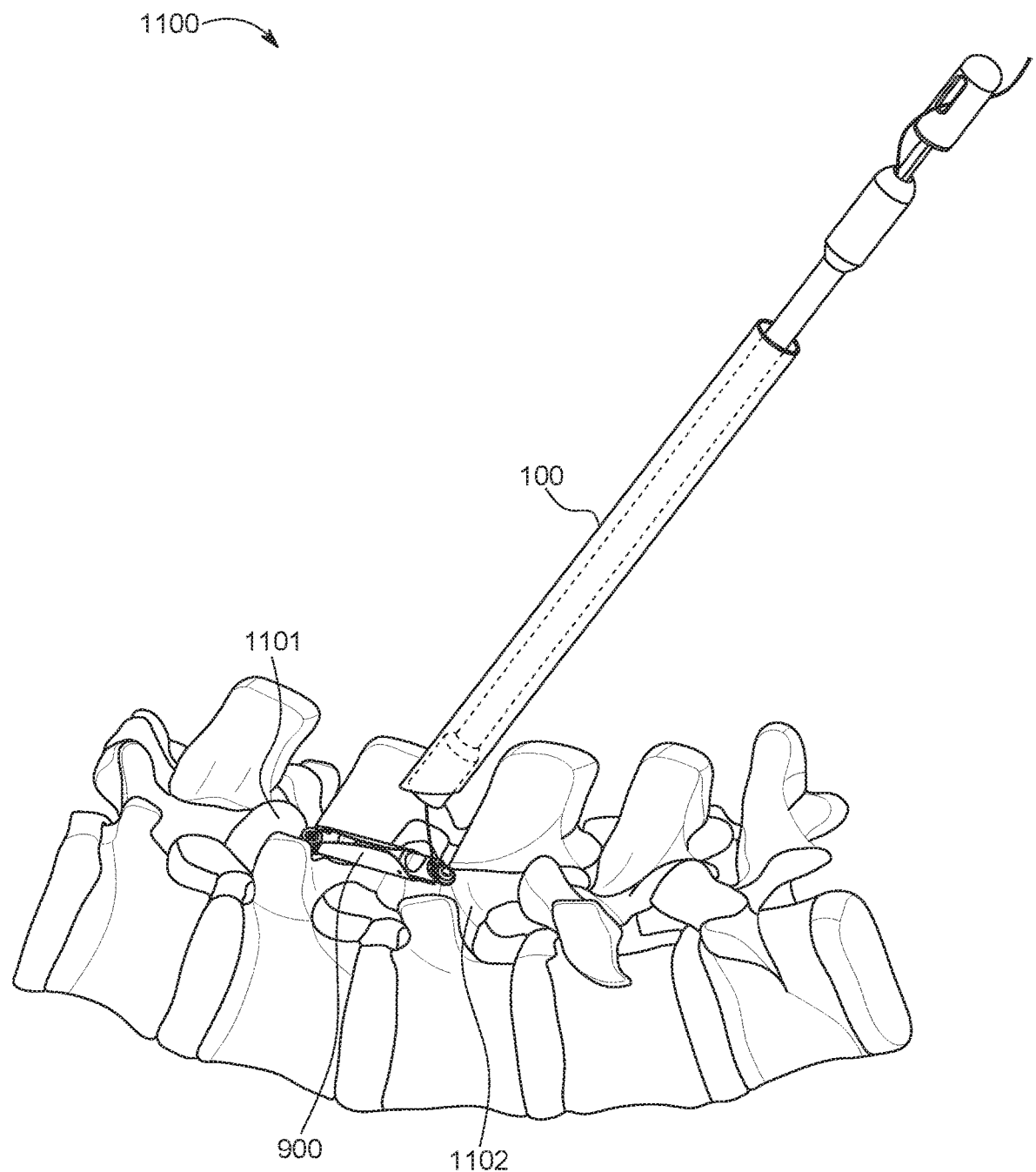
FIG. 20B is an isometric view of the section of vertebrae with the graft construct completely extruded from the slotted cannula.

For example, as shown in FIG. 20B, graft construct 900 may be completely extruded from cavity 105 of slotted cannula 100, and may extend from first spinal segment 1101 to second spinal segment 1102. In this way, the surgeon may attach, using slotted cannula 100, suture 800 to second anchor assembly 402 to permit graft construct 900 to be anchored between first anchor assembly 401 and second anchor assembly 402, as described below.

As further shown in FIG. 10, process 1000 may include attaching, using the slotted cannula, a second end of the suture to the second anchor assembly to permit a spinal fusion of the first spinal segment and the second spinal segment using the graft construct (block 1006). For example, the surgeon may attach, using slotted cannula 100, a second end of suture 800 to second anchor assembly 402 to permit a spinal fusion of first spinal segment 1101 and second spinal segment 1102. In other words, graft construct 900 may be anchored to first anchor assembly 401 and second anchor assembly 402 to permit first spinal segment 1101 and second spinal segment 1102 to fuse to graft construct 900.

The surgeon may, using suture tool 700, cause suture 800 to connect to second anchor assembly 402. For example, the surgeon may, using suture tool 700, wrap suture 800 around second anchor assembly 402. For example, suture 800 may wrap around anchor portion 403 of second anchor assembly 402 and be disposed between a bottom surface of washer 405 and a surface of second spinal segment 1102.

Figure 21A:
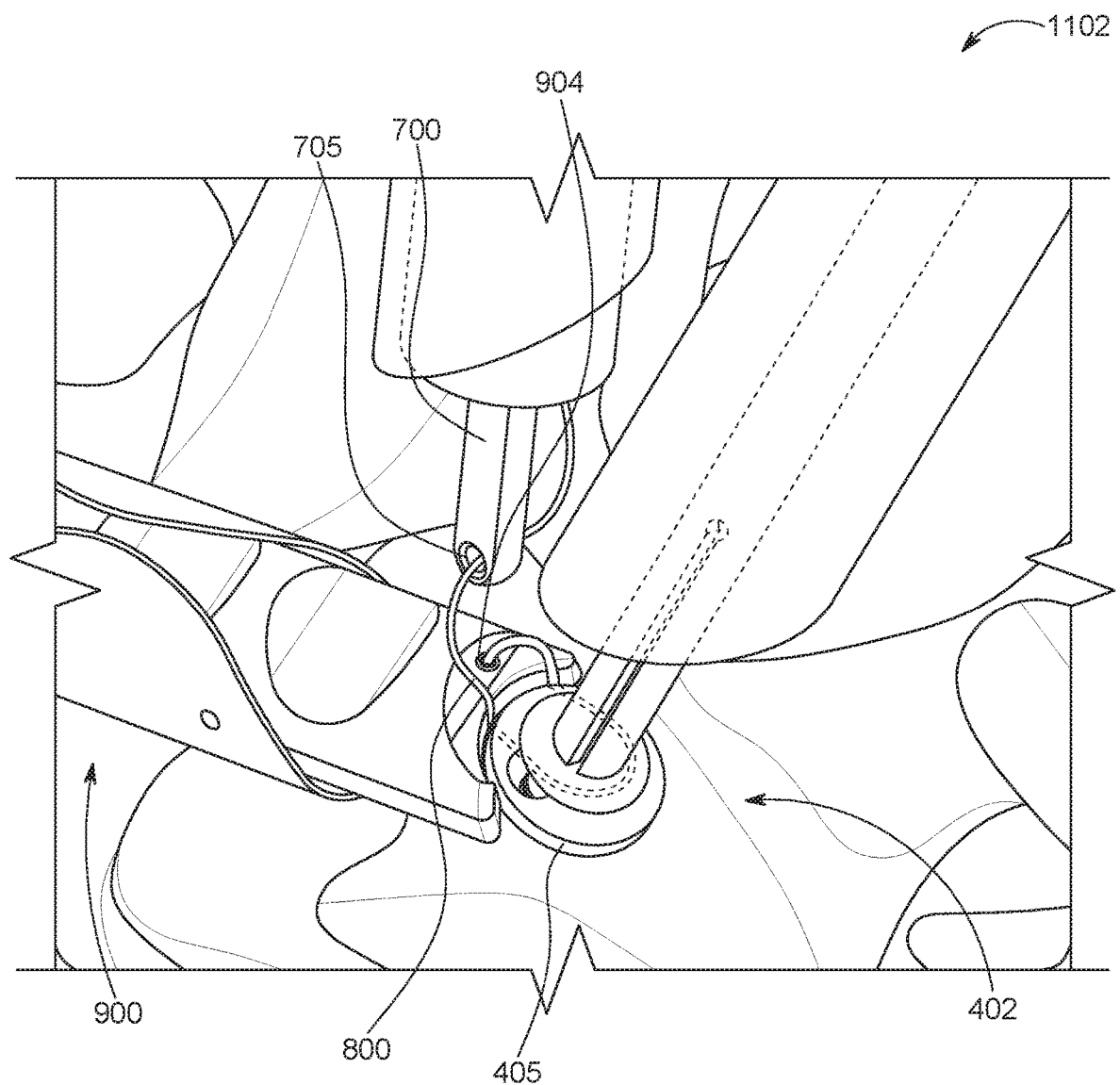
FIG. 21A is a close-up view of the second spinal segment with a suture wrapped around the second anchor assembly.

For example, as shown in FIG. 21A, suture 800 may extend from second connection mechanism 904 of graft construct 900, wrap around anchor portion 403 of second anchor assembly 402 and under washer 405 of second anchor assembly 402, and extend towards and be connected to suture tool 700 via distal connection mechanism 705.

Figure 21B:
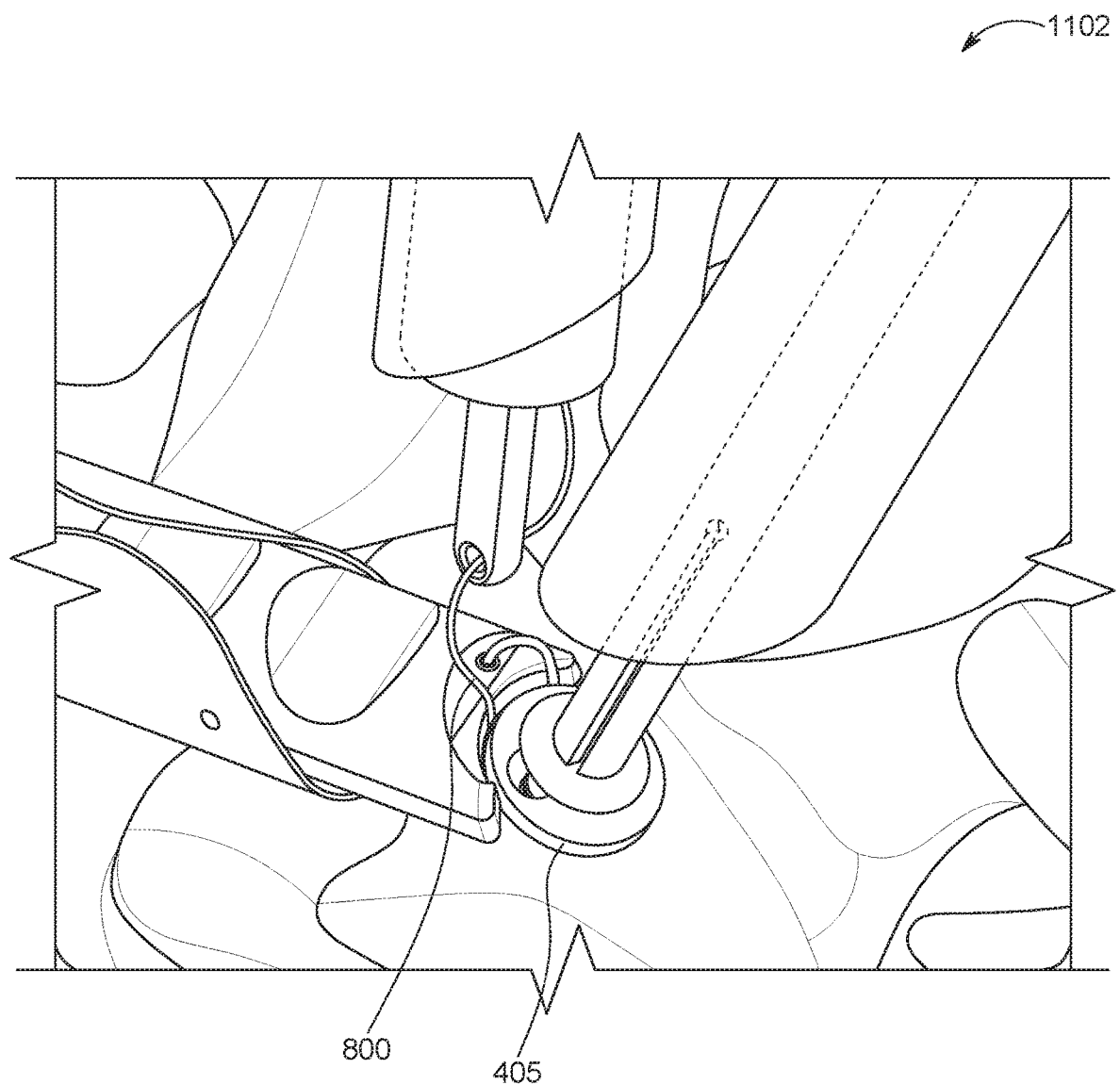
FIG. 21B is a close-up view of the second spinal segment with the second anchor assembly fastened to the second spinal segment.

The surgeon may, using anchor driver 500, fasten second anchor assembly 402 to second spinal segment 1102. For example, the surgeon may, using anchor driver 500, fasten second anchor assembly 402 such that suture 800 is anchored to second anchor assembly 402. For example, as shown in FIG. 21B, suture 800 may be disposed between a bottom surface of washer 405 of second anchor assembly 402 and a surface of second spinal segment 1102.

The surgeon may, using suture tool 700, sever suture 800 based on fastening second anchor assembly 402. Additionally, the surgeon may remove graft pusher 600 and suture tool 700 from cavity 105 of slotted cannula 100. Additionally, the surgeon may remove slotted cannula 100 from the patient and through the incision. Still further, the surgeon may close the incision.

Figure 22:
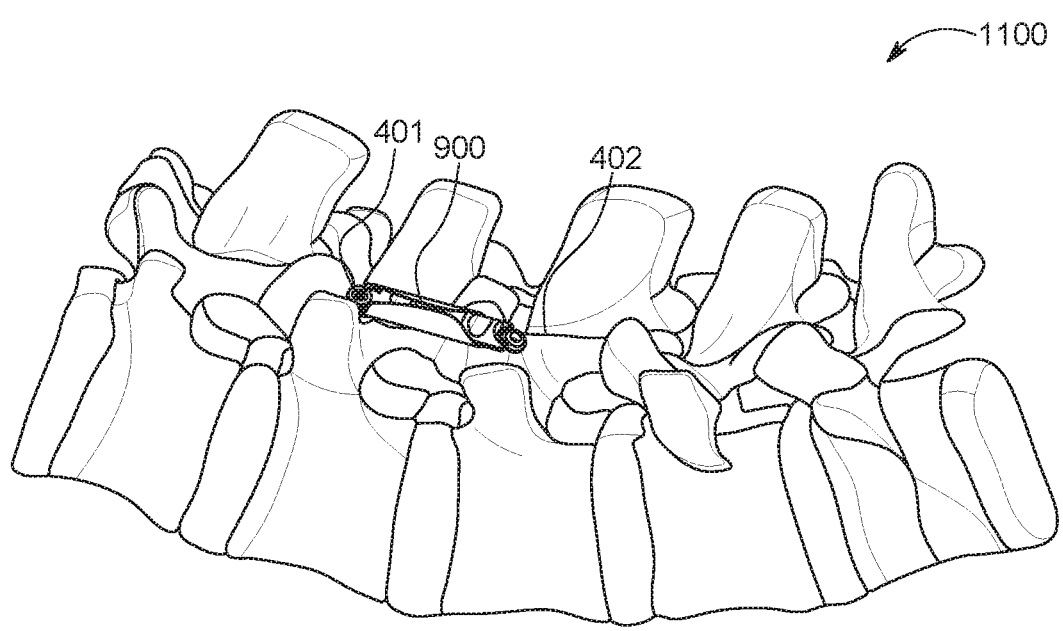
FIG. 22 is an isometric view of the section of vertebrae with the graft construct attached to the first anchor assembly and the second anchor assembly.

In this way, graft construct 900 may be disposed between and anchored to first anchor assembly 401 and second anchor assembly 402. For example, as shown in FIG. 22, graft construct 900 may be disposed between first anchor assembly 401 and second anchor assembly 402, thereby permitting spinal fusion of first spinal segment 1101 and second spinal segment 1102.

While FIG. 10 shows a single suture 800 being used to connect first anchor assembly 401, graft construct 900, and second anchor assembly 402, it should be understood that any number of sutures 800 may be used to connect the foregoing components.

As an alternative, the surgeon may prepare first spinal segment 1101 for endoscopic delivery of graft construct 900, and may insert first anchor assembly 401 into first spinal segment 1101 before preparing second spinal segment 1102 for endoscopic delivery of graft construct 900 and/or inserting second anchor assembly 402 into second spinal segment 1102.

Additionally, the surgeon may then prepare second spinal segment 1102 for endoscopic delivery of graft construct 900, and may then insert anchor assembly 402 into second spinal segment 1102. In other words, the surgeon may prepare a first site that corresponds to first spinal segment 1101, and may then prepare a second site that corresponds to second spinal segment 1102. In this way, a number of times that slotted cannula 100 is required to be translated from first spinal segment 1101 to second spinal segment 1102, and vice versa, is reduced.

As another alternative, the surgeon may connect graft construct 900 to first anchor assembly 401 before inserting first anchor assembly 401 into first spinal segment 1101. For example, first anchor assembly 401 may include a connected graft construct 900 that is connected to first anchor assembly 401 prior to first anchor assembly 401 being inserted into slotted cannula 100 and/or inserted into first spinal segment 1101. In this way, the surgeon may insert first anchor assembly 401, that includes the connected graft construct 900, into slotted cannula 100. Additionally, the surgeon may fasten first anchor assembly 401, that includes the connected graft construct 900, into first spinal segment 1101. Additionally, the surgeon may then extrude graft construct 900 from slotted cannula 100.

In this way, a number of steps is reduced because graft construct 900 is already attached to first anchor assembly 401 when first anchor assembly 401 is inserted into slotted cannula 100, thereby alleviating a need of the surgeon to attach graft construct 900 after first anchor assembly 401 is inserted into first spinal segment 1101.

As another alternative, first anchor assembly 401 may include graft construct 900. For example, first anchor assembly 401 and graft construct 900 may be connected, may be unitary, and/or the like. In other words, graft construct 900 and first anchor assembly 401 may be a unitary construct. In this way, the surgeon may insert and fasten first anchor assembly 401, that includes a connected graft construct 900, into first spinal segment 1101, thereby permitting the surgeon to extrude graft construct 900 without having to connect graft construct 900 to first anchor assembly 401. For example, and as shown in FIG. 17A, the surgeon may insert anchor driver 500 and first anchor assembly 401, that includes graft construct 900, into slotted cannula 100. Additionally, the surgeon may fasten, using anchor driver 500, first anchor assembly 401 into first spinal segment 1101. The surgeon may then remove anchor driver 500 from slotted cannula 100, and may insert graft pusher 600 into slotted cannula 100. The surgeon may then translate slotted cannula 100 and extrude, using graft pusher 600, graft construct 900 that is connected to first anchor assembly 401.

In this way, a number of steps required for endoscopic delivery of graft construct 900 is reduced because first anchor assembly 401 and graft construct 900 are already connected. Additionally, in this way, the consistency and/or accuracy of endoscopic delivery of graft construct 900 are improved because the performing surgeon is required to perform the reduced number of steps.

As another alternative, the surgeon may use multiple slotted cannulas 100 (or another type of cannula) when performing endoscopic delivery of graft construct 900. For example, the surgeon may use a first slotted cannula 100 for preparing first spinal segment 1101, and inserting and fastening first anchor assembly 401 into first spinal segment 1101. Additionally, the surgeon may use the first slotted cannula 100 to extrude graft construct 900.

Additionally, the surgeon may use a second slotted cannula 100 for preparing second spinal segment 1102, and inserting and fastening second anchor assembly 402 into second spinal segment 1102. Additionally, the surgeon may use the second slotted cannula 100 for attaching suture 800 to second anchor assembly 402. It should be understood that a single slotted cannula 100 or multiple slotted cannulas 100 may be used to perform the procedures described herein. In this way, a number of times slotted cannula 100 is translated between first spinal segment 1101 and second spinal segment 1102 is reduced.

As another alternative, multiple sutures 800 may be used to perform the procedures described herein. For example, a first suture 800 may connect first anchor assembly 401 and graft construct 900. Additionally, a second suture 800 may connect second anchor assembly 402 and graft construct 900. It should be understood that a single suture 800 or multiple sutures 800 may be used to perform the procedures described herein.

As another alternative, suture 800 may be connected to second anchor assembly 402 using different types of connection mechanisms or methods. For example, the surgeon may wrap suture 800 around second anchor assembly 402. Alternatively, the surgeon may thread suture 800 through washer 405 of second anchor assembly 402. Alternatively, the surgeon may wrap a loop portion of suture 800 around second anchor assembly 402.

As another alternative, multiple sutures 800 may be used in association with graft construct 900 and/or to remove sheath 907 from graft construct 900. For example, the surgeon may insert a first suture 800 that includes a suture needle through sheath 907 of graft construct 900. Additionally, the surgeon may pull suture 800 including the suture needle through sheath 907 until a knot portion of the first suture 800 is adjacent to sheath 907. The surgeon may then place a needle end of suture 800 through a hole in washer 405. The surgeon may then attach a second suture 800 to a portion of the first suture 800 that is disposed between washer 405 and the knot portion of the first suture 800. Additionally, the surgeon may pull a third suture 800 through slotted cannula 100 to close sheath 907 around graft construct 900, and may pull the second suture 800 through slotted cannula 100 to pull sheath 907 through slotted cannula 100, thereby removing sheath 907 from the incision.

Although FIG. 10 shows example blocks of process 1000, process 1000 may include additional blocks, fewer blocks, different blocks, or differently arranged blocks than those depicted in FIG. 10. Additionally, or alternatively, two or more of the blocks of process 1000 may be performed in parallel.

Some implementations described herein provide for endoscopic delivery of a graft through a slotted cannula. Additionally, some implementations described herein provide a minimally invasive technique for performing spinal fusion. In this way, some implementations described herein improve the safety, efficacy, consistency, etc. of spinal fusion procedures.

The foregoing disclosure provides illustration and description, but is not intended to be exhaustive or to limit the implementations to the precise form disclosed. Modifications and variations are possible in light of the above disclosure or may be acquired from practice of the implementations.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, and/or feature used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:
1. A cannula system, comprising:
   a cannula having a cavity;
   a slot extending longitudinally from a proximal end of the cannula to a distal end of the cannula;
   a channel that is offset from the cavity of the cannula, that extends longitudinally from the proximal end of the cannula to the distal end of the cannula, that is substantially planar, and that includes a width that corresponds to a width of a blade that is configured to translate within the channel; and
   the blade that is configured to be inserted into the channel, wherein the cannula system is configured to:
      permit a first guidewire to be inserted into a first spinal segment through the cavity of the cannula;
      permit a first anchor assembly to be inserted into the first spinal segment over the first guidewire while the blade, extending through the channel, is inserted into the first spinal segment;
      permit a second guidewire to be inserted into a second spinal segment through the cavity of the cannula;
      permit a second anchor assembly to be inserted into the second spinal segment through the cavity of the cannula and over the second guidewire;
      permit a graft construct to be extruded through the cavity of the cannula and extend from the first spinal segment to the second spinal segment; and
      translate, using the slot, from the first spinal segment to the second spinal segment without removing the first guidewire.

2. The cannula system of claim 1, further comprising:
a graft pusher configured to be inserted into the cavity of the cannula and to extrude the graft construct through the cavity of the cannula.

3. The cannula system of claim 1, further comprising:
a suture tool configured to be inserted into the cavity of the cannula and to attach the first anchor assembly, the second anchor assembly, and the graft construct using a suture.

4. The cannula system of claim 1, further comprising the first guidewire.

5. The cannula system of claim 1, wherein the cannula includes a diameter in the range of nine to eleven millimeters.

6. The cannula system of claim 1, wherein the first spinal segment is a first transverse process and the second spinal segment is a second transverse process.

* * * * *